(12) United States Patent
Mashiach et al.

(10) Patent No.: US 9,855,032 B2
(45) Date of Patent: *Jan. 2, 2018

(54) TRANSCUTANEOUS POWER CONVEYANCE DEVICE

(71) Applicant: Nyxoah SA, Mont-St-Guibert (BE)

(72) Inventors: Adi Mashiach, Tel Aviv (IL); Tim Ruytjens, Mortsel (BE); Itzik Mashiach, Kfar Yona (IL)

(73) Assignee: NYXOAH SA, Mont-St-Guibert (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/059,632

(22) Filed: Oct. 22, 2013

(65) Prior Publication Data

US 2014/0052219 A1 Feb. 20, 2014

Related U.S. Application Data

(63) Continuation of application No. 13/951,754, filed on Jul. 26, 2013.

(Continued)

(51) Int. Cl.
*A61N 1/36* (2006.01)
*A61B 17/04* (2006.01)
(Continued)

(52) U.S. Cl.
CPC ........ *A61B 17/0482* (2013.01); *A61N 1/0526* (2013.01); *A61N 1/0548* (2013.01);
(Continued)

(58) Field of Classification Search
CPC .... A61N 1/3787; A61N 1/08; A61N 1/37205; A61N 1/37223; H02J 7/025
(Continued)

(56) References Cited

U.S. PATENT DOCUMENTS 3,606,881 A * 9/1971 Woodson ............... 600/392
4,495,917 A 1/1985 Byers
(Continued)

FOREIGN PATENT DOCUMENTS

DE 10003338 A1 11/2000
DE 69527 T2 1/2003
(Continued)

OTHER PUBLICATIONS

PCT Search Report and Written Opinion for International Application No. PCT/IB13/02076, dated Apr. 24, 2014; 5 pgs.

*Primary Examiner* — Carl H Layno
*Assistant Examiner* — Erin M Piateski
(74) *Attorney, Agent, or Firm* — Finnegan, Henderson, Farabow, Garrett & Dunner LLP

(57) ABSTRACT

Some embodiments of the present disclosure may include a device for conveying power from a location external to a subject to a location within the subject The device may include a flexible carrier, an adhesive on a first side of the carrier, a coil of electrically conductive material associated with the flexible carrier, and a mechanical connector extending from a second side of the carrier opposite the adhesive. The mechanical connector may be configured to be received by and retained by a receiver associated with a housing configured for mounting on the carrier.

18 Claims, 16 Drawing Sheets

Related U.S. Application Data

(60) Provisional application No. 61/676,327, filed on Jul. 26, 2012.

(51) Int. Cl.
*A61N 1/05* (2006.01)
*A61N 1/378* (2006.01)
*A61N 1/372* (2006.01)
*H04B 5/00* (2006.01)
*H02J 7/02* (2016.01)
*A61N 1/375* (2006.01)
*H02J 50/12* (2016.01)

(52) U.S. Cl.
CPC ......... *A61N 1/0558* (2013.01); *A61N 1/3601* (2013.01); *A61N 1/36003* (2013.01); *A61N 1/3605* (2013.01); *A61N 1/3606* (2013.01); *A61N 1/3611* (2013.01); *A61N 1/36071* (2013.01); *A61N 1/36075* (2013.01); *A61N 1/36117* (2013.01); *A61N 1/36125* (2013.01); *A61N 1/36132* (2013.01); *A61N 1/36189* (2013.01); *A61N 1/375* (2013.01); *A61N 1/3787* (2013.01); *A61N 1/37229* (2013.01); *H02J 7/025* (2013.01); *H02J 50/12* (2016.02); *H04B 5/0037* (2013.01); *H04B 5/0031* (2013.01); *H04B 5/0081* (2013.01); *H04B 5/0093* (2013.01); *Y10T 29/49018* (2015.01)

(58) Field of Classification Search
USPC .......................................................... 607/61
See application file for complete search history.

(56) References Cited

U.S. PATENT DOCUMENTS

| | | | |
|---|---|---|---|
| 5,307,818 A * | 5/1994 | Segalowitz | 600/509 |
| 5,540,732 A | 7/1996 | Testerman | |
| 5,540,733 A | 7/1996 | Testerman et al. | |
| 5,546,952 A | 8/1996 | Erickson | |
| 5,549,655 A | 8/1996 | Erickson | |
| 5,591,216 A | 1/1997 | Testerman et al. | |
| 5,690,693 A | 11/1997 | Wang et al. | |
| 5,702,431 A | 12/1997 | Wang et al. | |
| 5,725,564 A | 3/1998 | Freed et al. | |
| 5,741,316 A | 4/1998 | Chen et al. | |
| 5,871,512 A | 2/1999 | Hemming et al. | |
| 5,873,898 A | 2/1999 | Hemming et al. | |
| 5,891,183 A * | 4/1999 | Zierhofer | 607/57 |
| 5,891,185 A | 4/1999 | Freed et al. | |
| 5,945,762 A | 8/1999 | Chen et al. | |
| 5,948,006 A | 9/1999 | Mann | |
| 5,987,359 A | 11/1999 | Freed et al. | |
| 6,009,878 A | 1/2000 | Weijand et al. | |
| RE36,626 E | 3/2000 | Henley | |
| 6,038,480 A | 3/2000 | Hrdlicka et al. | |
| 6,051,017 A | 4/2000 | Loeb et al. | |
| 6,058,330 A | 5/2000 | Borza | |
| 6,092,531 A | 7/2000 | Chen et al. | |
| 6,104,958 A | 8/2000 | Freed et al. | |
| 6,132,384 A | 10/2000 | Christopherson et al. | |
| 6,134,473 A | 10/2000 | Hemming et al. | |
| 6,144,881 A | 11/2000 | Hemming et al. | |
| 6,163,724 A | 12/2000 | Hemming et al. | |
| 6,175,764 B1 | 1/2001 | Loeb et al. | |
| 6,181,965 B1 | 1/2001 | Loeb et al. | |
| 6,185,455 B1 | 2/2001 | Loeb et al. | |
| 6,198,970 B1 | 3/2001 | Freed et al. | |
| 6,212,431 B1 | 4/2001 | Hahn et al. | |
| 6,214,032 B1 | 4/2001 | Loeb et al. | |
| 6,240,316 B1 | 5/2001 | Richmond et al. | |
| 6,240,318 B1 | 5/2001 | Phillips | |
| 6,251,126 B1 | 6/2001 | Ottenhoff et al. | |
| 6,269,269 B1 | 7/2001 | Ottenhoff et al. | |
| 6,275,737 B1 | 8/2001 | Mann | |
| 6,281,611 B1 | 8/2001 | Chen et al. | |
| 6,305,381 B1 | 10/2001 | Weijand et al. | |
| 6,324,430 B1 | 11/2001 | Zarinetchi et al. | |
| 6,324,431 B1 | 11/2001 | Zarinetchi et al. | |
| 6,331,744 B1 | 12/2001 | Chen et al. | |
| 6,344,021 B1 * | 2/2002 | Juster et al. | 600/15 |
| 6,345,202 B2 | 2/2002 | Richmond et al. | |
| 6,358,281 B1 | 3/2002 | Berrang et al. | |
| 6,389,318 B1 | 5/2002 | Zarinetchi et al. | |
| 6,430,444 B1 | 8/2002 | Borza | |
| 6,473,653 B1 | 10/2002 | Schallhorn et al. | |
| 6,477,425 B1 | 11/2002 | Nowick et al. | |
| 6,480,086 B1 * | 11/2002 | Kluge et al. | 336/200 |
| 6,496,733 B2 | 12/2002 | Zarinetchi et al. | |
| 6,530,876 B1 | 3/2003 | Spence | |
| 6,572,543 B1 | 6/2003 | Christopherson et al. | |
| 6,574,507 B1 | 6/2003 | Bonnet | |
| 6,587,725 B1 | 7/2003 | Durand et al. | |
| 6,622,049 B2 | 9/2003 | Penner et al. | |
| 6,628,989 B1 | 9/2003 | Penner et al. | |
| 6,636,767 B1 | 10/2003 | Knudson et al. | |
| 6,648,914 B2 | 11/2003 | Berrang et al. | |
| 6,657,351 B2 | 12/2003 | Chen et al. | |
| 6,684,105 B2 | 1/2004 | Cohen et al. | |
| 6,704,602 B2 | 3/2004 | Berg et al. | |
| 6,735,475 B1 | 5/2004 | Whitehurst et al. | |
| 6,736,771 B2 | 5/2004 | Sokolich et al. | |
| 6,738,671 B2 | 5/2004 | Christopherson et al. | |
| 6,764,446 B2 | 7/2004 | Wolinsky et al. | |
| 6,770,022 B2 | 8/2004 | Mechlenburg et al. | |
| 6,788,975 B1 | 9/2004 | Whitehurst et al. | |
| 6,839,594 B2 | 1/2005 | Cohen et al. | |
| 6,845,271 B2 | 1/2005 | Fang et al. | |
| 6,850,803 B1 | 2/2005 | Jimenez et al. | |
| 6,892,098 B2 | 5/2005 | Ayal et al. | |
| 6,907,295 B2 | 6/2005 | Gross et al. | |
| 6,928,324 B2 | 8/2005 | Park et al. | |
| 6,937,891 B2 | 8/2005 | Leinders et al. | |
| 7,024,248 B2 | 4/2006 | Penner et al. | |
| 7,027,860 B2 | 4/2006 | Bruninga et al. | |
| 7,039,468 B2 | 5/2006 | Freed et al. | |
| 7,054,691 B1 | 5/2006 | Kuzma et al. | |
| 7,103,408 B2 | 9/2006 | Haller et al. | |
| 7,120,992 B2 | 10/2006 | He et al. | |
| 7,132,173 B2 | 11/2006 | Daulton | |
| 7,146,221 B2 | 12/2006 | Krulevitch et al. | |
| 7,149,586 B2 | 12/2006 | Greenberg et al. | |
| 7,155,278 B2 | 12/2006 | King et al. | |
| 7,167,737 B2 | 1/2007 | Fujii et al. | |
| 7,177,698 B2 | 2/2007 | Klosterman et al. | |
| 7,181,287 B2 | 2/2007 | Greenberg | |
| 7,198,603 B2 | 4/2007 | Penner et al. | |
| 7,209,790 B2 | 4/2007 | Thompson et al. | |
| 7,212,862 B2 | 5/2007 | Park et al. | |
| 7,225,032 B2 | 5/2007 | Schmeling et al. | |
| 7,257,438 B2 | 8/2007 | Kinast | |
| 7,263,403 B2 | 8/2007 | Greenberg et al. | |
| 7,273,457 B2 | 9/2007 | Penner | |
| 7,277,749 B2 | 10/2007 | Gordon et al. | |
| 7,280,873 B2 | 10/2007 | Freed et al. | |
| 7,283,874 B2 | 10/2007 | Penner | |
| 7,286,881 B2 | 10/2007 | Schommer et al. | |
| 7,289,855 B2 | 10/2007 | Nghiem et al. | |
| 7,308,316 B2 | 12/2007 | Schommer | |
| 7,321,793 B2 | 1/2008 | Ben Ezra et al. | |
| 7,324,853 B2 | 1/2008 | Ayal et al. | |
| 7,338,522 B2 | 3/2008 | Greenberg et al. | |
| 7,346,398 B2 | 3/2008 | Gross et al. | |
| 7,351,921 B1 | 4/2008 | Haller et al. | |
| 7,367,935 B2 | 5/2008 | Mechlenburg et al. | |
| 7,392,091 B2 | 6/2008 | Bruinsma | |
| 7,392,092 B2 | 6/2008 | Li et al. | |
| 7,409,245 B1 | 8/2008 | Larson et al. | |
| 7,428,438 B2 | 9/2008 | Parramon et al. | |
| 7,437,193 B2 | 10/2008 | Parramon et al. | |
| 7,447,551 B2 | 11/2008 | Kuo et al. | |
| 7,482,783 B2 | 1/2009 | Schommer | |
| 7,483,750 B2 | 1/2009 | Greenberg et al. | |

(56) References Cited

U.S. PATENT DOCUMENTS

| | | |
|---|---|---|
| 7,489,966 B2 | 2/2009 | Leinders et al. |
| 7,493,172 B2 | 2/2009 | Whitehurst et al. |
| 7,499,754 B2 | 3/2009 | Greenberg et al. |
| 7,502,652 B2 | 3/2009 | Gaunt et al. |
| 7,512,443 B2 | 3/2009 | Phillips et al. |
| 7,527,621 B2 | 5/2009 | Greenberg et al. |
| 7,555,345 B2 | 6/2009 | Wahlstrand et al. |
| 7,561,922 B2 | 7/2009 | Cohen et al. |
| 7,587,241 B2 | 9/2009 | Parramon et al. |
| 7,599,744 B2 | 10/2009 | Giordano et al. |
| 7,610,065 B2 | 10/2009 | Vallapureddy et al. |
| 7,610,103 B2 | 10/2009 | Whitehurst et al. |
| 7,617,001 B2 | 11/2009 | Penner et al. |
| 7,628,750 B2 | 12/2009 | Cohen et al. |
| 7,630,771 B2 | 12/2009 | Cauller |
| 7,631,424 B2 | 12/2009 | Greenberg et al. |
| 7,634,317 B2 | 12/2009 | Ben-David et al. |
| 7,636,602 B2 | 12/2009 | Baru Fassio et al. |
| 7,640,061 B2 | 12/2009 | He et al. |
| 7,641,619 B2 | 1/2010 | Penner |
| 7,647,097 B2 | 1/2010 | Flaherty et al. |
| 7,647,112 B2 | 1/2010 | Tracey et al. |
| 7,660,632 B2 | 2/2010 | Kirby et al. |
| 7,668,580 B2 | 2/2010 | Shin et al. |
| 7,668,602 B2 | 2/2010 | Ben-David et al. |
| 7,672,728 B2 | 3/2010 | Libbus et al. |
| 7,680,538 B2 | 3/2010 | Durand et al. |
| 7,684,866 B2 | 3/2010 | Fowler et al. |
| 7,711,435 B2 | 5/2010 | Schommer |
| 7,720,547 B2 | 5/2010 | Denker et al. |
| 7,725,195 B2 | 5/2010 | Lima et al. |
| 7,734,355 B2 | 6/2010 | Cohen et al. |
| 7,756,587 B2 | 7/2010 | Penner et al. |
| 7,766,216 B2 | 8/2010 | Daulton |
| 7,769,461 B2 | 8/2010 | Whitehurst et al. |
| 7,774,069 B2 | 8/2010 | Olson et al. |
| 7,778,702 B2 | 8/2010 | Ben-David et al. |
| 7,778,703 B2 | 8/2010 | Gross et al. |
| 7,778,711 B2 | 8/2010 | Ben-David et al. |
| 7,781,683 B2 | 8/2010 | Haller et al. |
| 7,797,050 B2 | 9/2010 | Libbus et al. |
| 7,805,203 B2 | 9/2010 | Ben-David et al. |
| 7,809,442 B2 | 10/2010 | Bolea et al. |
| 7,810,233 B2 | 10/2010 | Krulevitch et al. |
| 7,822,480 B2 | 10/2010 | Park et al. |
| 7,831,308 B2 | 11/2010 | Rezai et al. |
| 7,836,888 B2 | 11/2010 | Hegde et al. |
| 7,844,346 B2 | 11/2010 | Cohen et al. |
| 7,845,357 B2 | 12/2010 | Buscemi et al. |
| 7,881,800 B2 | 2/2011 | Daly et al. |
| 7,882,842 B2 | 2/2011 | Bhat et al. |
| 7,885,709 B2 | 2/2011 | Ben-David |
| 7,885,711 B2 | 2/2011 | Ben-Ezra et al. |
| 7,887,493 B2 | 2/2011 | Stahmann et al. |
| 7,890,178 B2 | 2/2011 | Testerman et al. |
| 7,890,185 B2 | 2/2011 | Cohen et al. |
| 7,890,193 B2 | 2/2011 | Tingey |
| 7,894,909 B2 | 2/2011 | Greenberg et al. |
| 7,904,151 B2 | 3/2011 | Ben-David et al. |
| 7,904,163 B2 | 3/2011 | Greenberg et al. |
| 7,904,167 B2 | 3/2011 | Klosterman et al. |
| 7,904,176 B2 | 3/2011 | Ben-Ezra et al. |
| 7,908,008 B2 | 3/2011 | Ben-David et al. |
| 7,909,037 B2 | 3/2011 | Hegde et al. |
| 7,909,038 B2 | 3/2011 | Hegde et al. |
| 7,925,356 B2 | 4/2011 | Li et al. |
| 7,930,031 B2 | 4/2011 | Penner |
| RE42,378 E | 5/2011 | Wolinsky et al. |
| 7,937,159 B2 | 5/2011 | Lima et al. |
| 7,945,334 B2 | 5/2011 | Jimenez et al. |
| 7,962,211 B2 * | 6/2011 | Torgerson et al. ............ 607/33 |
| 7,970,479 B2 | 6/2011 | Goroszeniuk |
| 7,974,693 B2 | 7/2011 | Ben-David et al. |
| 7,979,126 B2 | 7/2011 | Payne et al. |
| 7,979,128 B2 | 7/2011 | Tehrani et al. |
| 7,979,137 B2 | 7/2011 | Tracey et al. |
| 7,980,248 B2 | 7/2011 | Hegde et al. |
| 7,991,478 B2 | 8/2011 | Greenberg et al. |
| 8,005,542 B2 | 8/2011 | Ben-Ezra et al. |
| 8,005,545 B2 | 8/2011 | Ben-David et al. |
| 8,010,205 B2 | 8/2011 | Rahman et al. |
| 8,014,878 B2 | 9/2011 | Greenberg et al. |
| 8,024,044 B2 | 9/2011 | Kirby et al. |
| 8,024,047 B2 | 9/2011 | Olson et al. |
| 8,027,735 B1 | 9/2011 | Tziviskos et al. |
| 8,032,227 B2 | 10/2011 | Parramon et al. |
| 8,035,255 B2 | 10/2011 | Kurs et al. |
| 8,036,745 B2 | 10/2011 | Ben-David et al. |
| 8,036,752 B2 | 10/2011 | Greenberg et al. |
| 8,060,197 B2 | 11/2011 | Ben-David et al. |
| 8,060,211 B2 | 11/2011 | Greenberg et al. |
| 8,065,021 B2 | 11/2011 | Gross et al. |
| 8,074,655 B2 | 12/2011 | Sanders |
| 8,078,284 B2 | 12/2011 | Greenberg et al. |
| 8,086,318 B2 | 12/2011 | Strother et al. |
| 8,115,618 B2 | 2/2012 | Robertson et al. |
| 8,116,875 B2 | 2/2012 | Osypka et al. |
| 8,116,881 B2 | 2/2012 | Cohen et al. |
| 8,122,596 B2 | 2/2012 | Krulevitch et al. |
| 8,126,562 B2 | 2/2012 | Fowler et al. |
| 8,127,424 B2 | 3/2012 | Haller et al. |
| 8,131,375 B2 | 3/2012 | Greenberg et al. |
| 8,140,167 B2 | 3/2012 | Donders et al. |
| 8,160,696 B2 | 4/2012 | Bendett et al. |
| 8,165,695 B2 | 4/2012 | DiUbaldi et al. |
| 8,170,680 B2 | 5/2012 | Ameri |
| 8,170,681 B2 | 5/2012 | Jimenez et al. |
| 8,174,460 B2 | 5/2012 | Larson et al. |
| 8,175,714 B2 | 5/2012 | Greenberg et al. |
| 8,175,716 B2 | 5/2012 | Rahman et al. |
| 8,180,460 B2 | 5/2012 | Nevsmith et al. |
| 8,185,212 B2 | 5/2012 | Carbunaru et al. |
| 8,204,591 B2 | 6/2012 | Ben-David et al. |
| 8,214,009 B2 | 7/2012 | Shin et al. |
| 8,214,045 B2 | 7/2012 | Kronich et al. |
| 8,220,467 B2 | 7/2012 | Sanders |
| 8,224,444 B2 | 7/2012 | Ben-David et al. |
| 8,224,449 B2 | 7/2012 | Carbunaru et al. |
| 8,229,567 B2 | 7/2012 | Phillips et al. |
| 8,238,975 B2 | 8/2012 | Vallapureddy et al. |
| 8,241,950 B2 | 8/2012 | Pellinen et al. |
| 8,249,713 B2 | 8/2012 | Fang et al. |
| 8,249,723 B2 | 8/2012 | McCreery |
| 8,256,425 B2 | 9/2012 | Bagley et al. |
| 8,260,432 B2 | 9/2012 | DiGiore et al. |
| 8,260,439 B2 | 9/2012 | Diubaldi et al. |
| 8,265,763 B2 | 9/2012 | Fahey |
| 8,265,770 B2 | 9/2012 | Toy et al. |
| 8,267,708 B1 | 9/2012 | Sochor |
| 8,285,381 B2 | 10/2012 | Fahey |
| 8,295,936 B2 | 10/2012 | Wahlstrand et al. |
| 8,301,261 B2 | 10/2012 | Bruinsma |
| 8,311,645 B2 | 11/2012 | Bolea et al. |
| 8,336,553 B2 | 12/2012 | Bhat et al. |
| 8,352,026 B2 | 1/2013 | DiUbaldi |
| 8,359,108 B2 | 1/2013 | McCreery |
| 8,369,957 B2 | 2/2013 | Greenberg et al. |
| 8,381,735 B2 | 2/2013 | Buscemi et al. |
| 8,386,046 B2 | 2/2013 | Tesfayesus et al. |
| 8,386,048 B2 | 2/2013 | McClure et al. |
| 8,386,056 B2 | 2/2013 | Ben David et al. |
| 8,391,991 B2 | 3/2013 | Rahman et al. |
| 8,406,886 B2 | 3/2013 | Gaunt et al. |
| 8,408,213 B2 | 4/2013 | Sanders |
| 8,417,343 B2 | 4/2013 | Bolea et al. |
| 8,428,725 B2 | 4/2013 | Meadows et al. |
| 8,428,727 B2 | 4/2013 | Bolea et al. |
| 8,428,746 B2 | 4/2013 | DiGiore et al. |
| 8,433,403 B2 | 4/2013 | Fahey |
| 8,447,410 B2 | 5/2013 | Greenberg et al. |
| 8,457,758 B2 | 6/2013 | Olson et al. |
| 8,463,383 B2 | 6/2013 | Sakai et al. |
| 8,463,394 B2 | 6/2013 | Forsell |
| 8,463,395 B2 | 6/2013 | Forsell |

(56) References Cited

U.S. PATENT DOCUMENTS

| | | |
|---|---|---|
| 8,473,025 B2 | 6/2013 | Shin et al. |
| 8,489,200 B2 | 7/2013 | Zarinetchi et al. |
| 8,494,641 B2 | 7/2013 | Boling et al. |
| 8,494,655 B2 | 7/2013 | Ayal et al. |
| 8,498,712 B2 | 7/2013 | Bolea et al. |
| 8,498,716 B2 | 7/2013 | Chen et al. |
| 8,509,909 B2 | 8/2013 | Figueiredo et al. |
| 8,509,911 B2 | 8/2013 | Li et al. |
| 8,510,939 B2 | 8/2013 | Greenberg et al. |
| 8,515,544 B2 | 8/2013 | Daly et al. |
| 8,532,787 B2 | 9/2013 | Lambert et al. |
| 8,538,503 B2 | 9/2013 | Kumar et al. |
| 8,540,631 B2 | 9/2013 | Penner et al. |
| 8,540,632 B2 | 9/2013 | Robertson et al. |
| 8,543,216 B2 | 9/2013 | Carbunaru et al. |
| 8,560,046 B2 | 10/2013 | Kumar et al. |
| 8,565,896 B2 | 10/2013 | Ben-David et al. |
| 8,571,651 B2 | 10/2013 | Ben-Ezra et al. |
| 8,571,653 B2 | 10/2013 | Ben-David et al. |
| 8,571,679 B2 | 10/2013 | Parramon et al. |
| 8,577,460 B2 | 11/2013 | Penner |
| 8,577,465 B2 * | 11/2013 | Mashiach ............ 607/42 |
| 8,577,466 B2 * | 11/2013 | Mashiach ............ 607/42 |
| 8,578,937 B2 | 11/2013 | Bhat et al. |
| 8,583,256 B2 | 11/2013 | Tracey et al. |
| 8,588,901 B2 | 11/2013 | Fahey |
| 8,588,924 B2 | 11/2013 | Dion |
| 8,588,930 B2 | 11/2013 | DiUbaldi et al. |
| 8,600,517 B2 | 12/2013 | Forsell |
| 8,612,013 B2 | 12/2013 | Forsell |
| 8,612,014 B2 | 12/2013 | Rahman et al. |
| 8,615,294 B2 | 12/2013 | Ben-David et al. |
| 8,620,437 B2 | 12/2013 | Wahlstrand et al. |
| 8,620,447 B2 | 12/2013 | D'Ambrosio et al. |
| 8,626,302 B2 | 1/2014 | Bennett et al. |
| 8,626,304 B2 | 1/2014 | Bolea et al. |
| 8,639,344 B2 | 1/2014 | Greenberg et al. |
| 8,639,354 B2 | 1/2014 | Bolea et al. |
| 8,644,939 B2 | 2/2014 | Wilson et al. |
| 8,655,451 B2 | 2/2014 | Klosterman et al. |
| 8,657,756 B2 | 2/2014 | Stahmann et al. |
| 8,658,465 B2 | 2/2014 | Pellinen et al. |
| 8,668,643 B2 | 3/2014 | Kinast |
| 8,670,835 B2 | 3/2014 | Park et al. |
| 8,676,332 B2 | 3/2014 | Fahey |
| 8,700,177 B2 | 4/2014 | Strother et al. |
| 8,703,537 B2 | 4/2014 | Pellinen et al. |
| 8,718,758 B2 | 5/2014 | Wagner et al. |
| 8,718,783 B2 | 5/2014 | Bolea et al. |
| 8,718,791 B2 | 5/2014 | Ben-David et al. |
| 8,725,271 B2 | 5/2014 | Ayal et al. |
| 8,738,148 B2 | 5/2014 | Olson et al. |
| 8,744,582 B2 | 6/2014 | Wahlstrand et al. |
| 8,744,589 B2 | 6/2014 | Bolea et al. |
| 8,751,003 B2 | 6/2014 | DiUbaldi et al. |
| 8,751,005 B2 | 6/2014 | Meadows et al. |
| 8,774,943 B2 | 7/2014 | McCreery |
| 8,788,046 B2 | 7/2014 | Bennett et al. |
| 8,788,047 B2 | 7/2014 | Bennett et al. |
| 8,788,048 B2 | 7/2014 | Bennett et al. |
| 8,798,763 B2 | 8/2014 | Forsell |
| 8,813,753 B2 | 8/2014 | Bhat et al. |
| 8,825,173 B2 | 9/2014 | Forsell |
| 8,855,771 B2 | 10/2014 | Tesfayesus et al. |
| 8,862,232 B2 | 10/2014 | Zarinetchi et al. |
| 8,880,184 B2 | 11/2014 | Phillips et al. |
| 8,886,304 B2 | 11/2014 | Wagner et al. |
| 8,886,322 B2 | 11/2014 | Meadows et al. |
| 8,886,325 B2 | 11/2014 | Boling et al. |
| 8,886,329 B2 | 11/2014 | Greenberg et al. |
| 8,886,337 B2 | 11/2014 | Bennett et al. |
| 8,892,200 B2 | 11/2014 | Wagner et al. |
| 8,892,205 B2 | 11/2014 | Miller, III et al. |
| 8,892,210 B2 | 11/2014 | Fahey |
| 8,897,871 B2 | 11/2014 | Wagner et al. |
| 8,903,495 B2 | 12/2014 | Greenberg et al. |
| 8,903,502 B2 | 12/2014 | Perryman et al. |
| 8,914,129 B2 | 12/2014 | Parramon et al. |
| 8,925,551 B2 | 1/2015 | Sanders |
| 8,929,979 B2 | 1/2015 | Wagner et al. |
| 8,929,986 B2 | 1/2015 | Parker et al. |
| 8,934,972 B2 | 1/2015 | Penner |
| 8,954,153 B2 | 2/2015 | Boggs, II |
| 8,965,523 B2 | 2/2015 | Forsell |
| 8,965,525 B2 | 2/2015 | Forsell |
| 8,965,535 B2 | 2/2015 | Dunlay et al. |
| 8,972,021 B2 | 3/2015 | Edgell et al. |
| 8,977,354 B2 | 3/2015 | Wagner et al. |
| 8,983,611 B2 | 3/2015 | Mokelke et al. |
| 9,002,451 B2 | 4/2015 | Staunton et al. |
| 9,026,222 B2 | 5/2015 | Forsell |
| 9,031,654 B2 | 5/2015 | Meadows et al. |
| 9,042,991 B2 | 5/2015 | Reed et al. |
| 9,061,134 B2 | 6/2015 | Askin, III et al. |
| 9,072,886 B2 | 7/2015 | Gaunt et al. |
| 9,079,041 B2 | 7/2015 | Park et al. |
| 9,079,043 B2 | 7/2015 | Stark et al. |
| 9,089,690 B2 | 7/2015 | Greenberg et al. |
| 9,113,838 B2 | 8/2015 | Tesfayesus et al. |
| 9,125,290 B2 | 9/2015 | Greenberg et al. |
| 9,126,039 B2 | 9/2015 | Fahey |
| 9,149,228 B2 | 10/2015 | Kinast |
| 9,149,386 B2 | 10/2015 | Fahey et al. |
| 9,149,628 B2 | 10/2015 | Wahlstrand et al. |
| 9,162,071 B2 | 10/2015 | Parramon et al. |
| 9,186,496 B2 | 11/2015 | Greenberg et al. |
| 9,186,511 B2 | 11/2015 | Bolea |
| 9,205,258 B2 | 12/2015 | Simon et al. |
| 9,205,262 B2 | 12/2015 | Bolea et al. |
| 9,227,076 B2 | 1/2016 | Sharma et al. |
| 9,233,258 B2 | 1/2016 | Simon et al. |
| 9,241,649 B2 | 1/2016 | Kumar et al. |
| 9,242,106 B2 | 1/2016 | Klosterman et al. |
| 9,248,289 B2 | 2/2016 | Bennett et al. |
| 9,272,081 B2 | 3/2016 | Cameron et al. |
| 9,289,142 B2 | 3/2016 | Kong et al. |
| 9,302,104 B2 | 4/2016 | Fahey |
| 9,308,370 B2 | 4/2016 | Lima et al. |
| 9,314,615 B2 | 4/2016 | Neysmith et al. |
| 9,314,618 B2 | 4/2016 | Imran et al. |
| 9,314,641 B2 | 4/2016 | Meadows et al. |
| 9,320,895 B2 | 4/2016 | Wagner et al. |
| 9,320,908 B2 | 4/2016 | Fletcher et al. |
| 9,339,647 B2 | 5/2016 | Strother et al. |
| 9,339,651 B2 | 5/2016 | Meadows et al. |
| 2002/0010495 A1 | 1/2002 | Freed et al. |
| 2002/0038138 A1 | 3/2002 | Zarinetchi et al. |
| 2002/0055763 A1 | 5/2002 | Zarinetchi et al. |
| 2002/0058971 A1 | 5/2002 | Zarinetchi et al. |
| 2002/0077572 A1 | 6/2002 | Fang et al. |
| 2002/0087204 A1 * | 7/2002 | Kung et al. ............ 607/61 |
| 2002/0177884 A1 | 11/2002 | Ahn et al. |
| 2002/0188333 A1 * | 12/2002 | Nowick et al. ............ 607/61 |
| 2003/0030342 A1 | 2/2003 | Chen et al. |
| 2003/0050549 A1 * | 3/2003 | Sochor ............ 600/378 |
| 2003/0093128 A1 | 5/2003 | Freed et al. |
| 2003/0097165 A1 | 5/2003 | Krulevitch et al. |
| 2003/0139782 A1 * | 7/2003 | Duncan et al. ............ 607/48 |
| 2004/0015096 A1 * | 1/2004 | Mok et al. ............ 600/547 |
| 2004/0064166 A1 | 4/2004 | Thompson et al. |
| 2004/0073272 A1 | 4/2004 | Knudson et al. |
| 2004/0098068 A1 | 5/2004 | Carbunaru et al. |
| 2004/0172104 A1 | 9/2004 | Berg et al. |
| 2004/0172115 A1 | 9/2004 | Miazga et al. |
| 2004/0199237 A1 * | 10/2004 | Mills et al. ............ 607/152 |
| 2004/0236387 A1 | 11/2004 | Fang et al. |
| 2005/0060030 A1 | 3/2005 | Lashinski et al. |
| 2005/0065553 A1 | 3/2005 | Ben Ezra et al. |
| 2005/0085874 A1 | 4/2005 | Davis et al. |
| 2005/0101853 A1 * | 5/2005 | Rowe et al. ............ 600/394 |
| 2005/0102006 A1 | 5/2005 | Whitehurst et al. |
| 2005/0119605 A1 * | 6/2005 | Sohn ............ 604/21 |
| 2005/0128038 A1 * | 6/2005 | Hyvonen ............ 336/182 |
| 2005/0177067 A1 | 8/2005 | Tracey et al. |

(56) References Cited

U.S. PATENT DOCUMENTS

| | | | |
|---|---|---|---|
| 2005/0267547 A1 | 12/2005 | Knudson et al. | |
| 2005/0283203 A1* | 12/2005 | Flaherty et al. | 607/48 |
| 2005/0288743 A1 | 12/2005 | Ahn et al. | |
| 2006/0009816 A1 | 1/2006 | Fang et al. | |
| 2006/0044188 A1* | 3/2006 | Tsai et al. | 343/700 MS |
| 2006/0064140 A1 | 3/2006 | Whitehurst et al. | |
| 2006/0090762 A1 | 5/2006 | Hegde et al. | |
| 2006/0116739 A1 | 6/2006 | Betser et al. | |
| 2006/0190056 A1 | 8/2006 | Fowler et al. | |
| 2006/0202789 A1* | 9/2006 | Hyvonen | 336/200 |
| 2006/0264835 A1 | 11/2006 | Nielsen et al. | |
| 2006/0270968 A1 | 11/2006 | Greenberg et al. | |
| 2007/0055324 A1 | 3/2007 | Thompson et al. | |
| 2007/0106167 A1* | 5/2007 | Kinast | 600/509 |
| 2007/0144535 A1 | 6/2007 | Hegde et al. | |
| 2007/0179584 A1* | 8/2007 | Gliner | 607/152 |
| 2007/0233204 A1 | 10/2007 | Lima et al. | |
| 2007/0261701 A1 | 11/2007 | Sanders | |
| 2008/0004676 A1* | 1/2008 | Osypka et al. | 607/59 |
| 2008/0046016 A1 | 2/2008 | Ben-David et al. | |
| 2008/0047566 A1 | 2/2008 | Hegde et al. | |
| 2008/0057179 A1 | 3/2008 | Greenberg et al. | |
| 2008/0058898 A1 | 3/2008 | Greenberg et al. | |
| 2008/0064946 A1 | 3/2008 | Greenberg et al. | |
| 2008/0078411 A1 | 4/2008 | Buscemi et al. | |
| 2008/0078412 A1 | 4/2008 | Buscemi et al. | |
| 2008/0082147 A1 | 4/2008 | Dai et al. | |
| 2008/0091241 A1 | 4/2008 | Ben-Ezra et al. | |
| 2008/0091245 A1 | 4/2008 | Ben-Ezra et al. | |
| 2008/0103545 A1* | 5/2008 | Bolea et al. | 607/42 |
| 2008/0109045 A1 | 5/2008 | Gross et al. | |
| 2008/0119898 A1 | 5/2008 | Ben-David et al. | |
| 2008/0125819 A1 | 5/2008 | Ben-David et al. | |
| 2008/0125827 A1 | 5/2008 | Ben-David et al. | |
| 2008/0132964 A1 | 6/2008 | Cohen et al. | |
| 2008/0147137 A1 | 6/2008 | Cohen et al. | |
| 2008/0147146 A1* | 6/2008 | Wahlgren et al. | 607/61 |
| 2008/0161874 A1 | 7/2008 | Bennett et al. | |
| 2008/0177351 A1 | 7/2008 | Fang et al. | |
| 2008/0288026 A1* | 11/2008 | Cross et al. | 607/60 |
| 2008/0300657 A1 | 12/2008 | Stultz | |
| 2009/0005845 A1 | 1/2009 | David et al. | |
| 2009/0011922 A1* | 1/2009 | de Rochemont | 501/137 |
| 2009/0038623 A1 | 2/2009 | Farbarik et al. | |
| 2009/0069866 A1 | 3/2009 | Farbarik et al. | |
| 2009/0078275 A1 | 3/2009 | Hegde et al. | |
| 2009/0173351 A1 | 7/2009 | Sahin et al. | |
| 2009/0182394 A1* | 7/2009 | Bachinski | 607/59 |
| 2009/0233491 A1 | 9/2009 | Barker et al. | |
| 2009/0240314 A1 | 9/2009 | Kong et al. | |
| 2009/0318793 A1* | 12/2009 | Datta et al. | 600/391 |
| 2010/0010603 A1 | 1/2010 | Ben-David et al. | |
| 2010/0016929 A1 | 1/2010 | Prochazka | |
| 2010/0036445 A1* | 2/2010 | Sakai et al. | 607/2 |
| 2010/0049028 A1* | 2/2010 | Shin et al. | 600/391 |
| 2010/0063568 A1 | 3/2010 | Staunton et al. | |
| 2010/0069994 A1 | 3/2010 | Cauller | |
| 2010/0075527 A1* | 3/2010 | McIntire et al. | 439/357 |
| 2010/0090824 A1* | 4/2010 | Rowell et al. | 340/539.11 |
| 2010/0131029 A1 | 5/2010 | Durand et al. | |
| 2010/0152809 A1 | 6/2010 | Boggs, II | |
| 2010/0174341 A1 | 7/2010 | Bolea et al. | |
| 2010/0198103 A1 | 8/2010 | Meadows et al. | |
| 2010/0217353 A1 | 8/2010 | Forsell | |
| 2010/0241195 A1 | 9/2010 | Meadows et al. | |
| 2010/0268305 A1* | 10/2010 | Olson et al. | 607/61 |
| 2010/0298842 A1 | 11/2010 | Daglow et al. | |
| 2010/0312188 A1* | 12/2010 | Robertson et al. | 604/156 |
| 2010/0319711 A1 | 12/2010 | Hegde et al. | |
| 2011/0009920 A1 | 1/2011 | Whitehurst et al. | |
| 2011/0071591 A1 | 3/2011 | Bolea et al. | |
| 2011/0082515 A1 | 4/2011 | Libbus et al. | |
| 2011/0112601 A1 | 5/2011 | Meadows et al. | |
| 2011/0152706 A1 | 6/2011 | Christopherson et al. | |
| 2011/0160794 A1 | 6/2011 | Bolea et al. | |
| 2011/0172733 A1 | 7/2011 | Lima et al. | |
| 2011/0202119 A1 | 8/2011 | Ni et al. | |
| 2011/0213438 A1* | 9/2011 | Lima et al. | 607/42 |
| 2011/0218408 A1 | 9/2011 | Green et al. | |
| 2011/0240037 A1 | 10/2011 | Hegde et al. | |
| 2011/0245734 A1 | 10/2011 | Wagner et al. | |
| 2011/0245892 A1* | 10/2011 | Kast et al. | 607/65 |
| 2011/0257495 A1 | 10/2011 | Hoss et al. | |
| 2011/0257701 A1* | 10/2011 | Strother et al. | 607/46 |
| 2011/0265322 A1 | 11/2011 | Greenberg et al. | |
| 2011/0275927 A1 | 11/2011 | Wagner et al. | |
| 2011/0288388 A1* | 11/2011 | Shah et al. | 600/347 |
| 2011/0319729 A1* | 12/2011 | Donnay et al. | 600/309 |
| 2012/0022609 A1 | 1/2012 | Bolea et al. | |
| 2012/0065701 A1 | 3/2012 | Cauller | |
| 2012/0104103 A1* | 5/2012 | Manzi | 235/492 |
| 2012/0109020 A1 | 5/2012 | Wagner et al. | |
| 2012/0139485 A1 | 6/2012 | Olson et al. | |
| 2012/0192874 A1 | 8/2012 | Bolea et al. | |
| 2012/0203318 A1* | 8/2012 | Mann et al. | 607/116 |
| 2012/0227748 A1 | 9/2012 | Sanders | |
| 2012/0286582 A1 | 11/2012 | Kim et al. | |
| 2012/0290055 A1 | 11/2012 | Boggs, II | |
| 2012/0303080 A1 | 11/2012 | Ben-David et al. | |
| 2012/0330126 A1* | 12/2012 | Hoppe et al. | 600/391 |
| 2013/0002423 A1 | 1/2013 | Robertson et al. | |
| 2013/0110195 A1 | 5/2013 | Fletcher et al. | |
| 2013/0116745 A1 | 5/2013 | Fletcher et al. | |
| 2013/0165996 A1 | 6/2013 | Meadows et al. | |
| 2013/0197615 A1 | 8/2013 | Rundle et al. | |
| 2013/0213404 A1* | 8/2013 | Leibitzki et al. | 128/207.14 |
| 2013/0218251 A1 | 8/2013 | Penner | |
| 2013/0238044 A1 | 9/2013 | Penner | |
| 2013/0238066 A1 | 9/2013 | Boggs, II et al. | |
| 2013/0274842 A1 | 10/2013 | Gaunt et al. | |
| 2013/0338452 A1 | 12/2013 | Robertson et al. | |
| 2014/0012342 A1 | 1/2014 | Penner et al. | |
| 2014/0046407 A1 | 2/2014 | Ben-Ezra et al. | |
| 2014/0058495 A1 | 2/2014 | Sakai et al. | |
| 2014/0121741 A1 | 5/2014 | Bennett et al. | |
| 2014/0152246 A1 | 6/2014 | Forsell | |
| 2014/0155959 A1 | 6/2014 | Forsell | |
| 2014/0163661 A1 | 6/2014 | Ben-David et al. | |
| 2014/0207220 A1 | 7/2014 | Boling et al. | |
| 2014/0214135 A1 | 7/2014 | Ben-David et al. | |
| 2014/0249361 A1 | 9/2014 | DiUbaldi et al. | |
| 2014/0323839 A1 | 10/2014 | McCreery | |
| 2014/0330340 A1 | 11/2014 | Bennett et al. | |
| 2014/0330356 A1 | 11/2014 | Bennett et al. | |
| 2014/0378740 A1 | 12/2014 | Wagner et al. | |
| 2015/0025613 A1 | 1/2015 | Nyberg, II et al. | |
| 2015/0039055 A1 | 2/2015 | Wagner et al. | |
| 2015/0039067 A1 | 2/2015 | Greenberg et al. | |
| 2015/0051678 A1 | 2/2015 | Reed et al. | |
| 2015/0066106 A1 | 3/2015 | Greenberg et al. | |
| 2015/0105702 A1 | 4/2015 | Wagner et al. | |
| 2015/0105840 A1 | 4/2015 | Boggs, II | |
| 2015/0119629 A1 | 4/2015 | Wagner et al. | |
| 2015/0134037 A1 | 5/2015 | Bennett et al. | |
| 2015/0142075 A1 | 5/2015 | Miller, III et al. | |
| 2015/0142120 A1 | 5/2015 | Papay | |
| 2015/0148713 A1 | 5/2015 | Wagner et al. | |
| 2015/0151123 A1 | 6/2015 | Wagner et al. | |
| 2015/0174409 A1 | 6/2015 | Parker et al. | |
| 2015/0264816 A1 | 9/2015 | Askin, III et al. | |
| 2015/0321004 A1 | 11/2015 | Reed et al. | |
| 2015/0321008 A1 | 11/2015 | Tesfayesus et al. | |
| 2015/0321018 A1 | 11/2015 | Fletcher et al. | |
| 2015/0328455 A1 | 11/2015 | Meadows et al. | |
| 2015/0374985 A1 | 12/2015 | Fahey | |
| 2015/0374998 A1 | 12/2015 | Fletcher et al. | |
| 2016/0001079 A1 | 1/2016 | Fletcher et al. | |
| 2016/0008608 A1 | 1/2016 | Boling et al. | |
| 2016/0022481 A1 | 1/2016 | Fahey et al. | |
| 2016/0030746 A1 | 2/2016 | Reed et al. | |
| 2016/0059011 A1 | 3/2016 | Bolea et al. | |
| 2016/0067396 A1 | 3/2016 | Stark et al. | |
| 2016/0089540 A1 | 3/2016 | Bolea | |
| 2016/0114174 A1 | 4/2016 | Colvin et al. | |

(56) References Cited

U.S. PATENT DOCUMENTS

| | | | |
|---|---|---|---|
| 2016/0114175 A1 | 4/2016 | Colvin et al. | |
| 2016/0114177 A1 | 4/2016 | Colvin et al. | |
| 2016/0135746 A1 | 5/2016 | Kumar et al. | |
| 2016/0144180 A1 | 5/2016 | Simon et al. | |

FOREIGN PATENT DOCUMENTS

| | | | | |
|---|---|---|---|---|
| DE | 69529951 T2 | 2/2004 | | |
| DE | 69722782 T2 | 2/2004 | | |
| DE | 69629238 T2 | 5/2004 | | |
| DE | 69532514 T2 | 10/2004 | | |
| DE | 69730842 T2 | 9/2005 | | |
| DE | 69927438 T2 | 6/2006 | | |
| DE | 69928748 T2 | 6/2006 | | |
| DE | 69636883 T2 | 10/2007 | | |
| DE | 60315327 T2 | 1/2008 | | |
| DE | 69535686 T2 | 1/2009 | | |
| DE | 112008001669 T5 | 5/2010 | | |
| DE | 202007019439 U1 | 9/2012 | | |
| EP | 0457525 | * 5/1991 | ........... H01R 13/625 | |
| EP | 0702977 B1 | 3/1996 | | |
| EP | 0706808 B1 | 4/1996 | | |
| EP | 0743076 B1 | 11/1996 | | |
| EP | 0814868 B1 | 1/1998 | | |
| EP | 0970713 B1 | 1/2000 | | |
| EP | 0998328 B1 | 5/2000 | | |
| EP | 1052935 B1 | 11/2000 | | |
| EP | 1175919 B1 | 1/2002 | | |
| EP | 1277491 B1 | 1/2003 | | |
| EP | 1306104 B1 | 5/2003 | | |
| EP | 1331969 B1 | 8/2003 | | |
| EP | 1389079 B1 | 2/2004 | | |
| EP | 1429837 B1 | 6/2004 | | |
| EP | 1446188 B1 | 8/2004 | | |
| EP | 1494753 B1 | 1/2005 | | |
| EP | 1507473 B1 | 2/2005 | | |
| EP | 1524007 A1 | 4/2005 | | |
| EP | 1545693 B1 | 6/2005 | | |
| EP | 1554012 B1 | 7/2005 | | |
| EP | 1608432 B1 | 12/2005 | | |
| EP | 1609502 A1 | 12/2005 | | |
| EP | 1613396 B1 | 1/2006 | | |
| EP | 1648559 B1 | 4/2006 | | |
| EP | 1675648 B1 | 7/2006 | | |
| EP | 1676526 B1 | 7/2006 | | |
| EP | 1682222 B1 | 7/2006 | | |
| EP | 1706178 B1 | 10/2006 | | |
| EP | 1750801 B1 | 2/2007 | | |
| EP | 1776922 A1 | 4/2007 | | |
| EP | 1861162 B1 | 12/2007 | | |
| EP | 1874397 A2 | 1/2008 | | |
| EP | 1897586 B1 | 3/2008 | | |
| EP | 1904153 B1 | 4/2008 | | |
| EP | 1907048 A2 | 4/2008 | | |
| EP | 1981583 B1 | 10/2008 | | |
| EP | 1981589 B1 | 10/2008 | | |
| EP | 2036588 B1 | 3/2009 | | |
| EP | 2040790 B1 | 4/2009 | | |
| EP | 2089100 B1 | 8/2009 | | |
| EP | 2116274 B1 | 11/2009 | | |
| EP | 2143465 B1 | 1/2010 | | |
| EP | 2167187 A2 | 3/2010 | | |
| EP | 2228095 A3 | 9/2010 | | |
| EP | 2243509 A1 | 10/2010 | | |
| EP | 2266164 B1 | 12/2010 | | |
| EP | 2272562 A1 | 1/2011 | | |
| EP | 2286871 B1 | 2/2011 | | |
| EP | 2289596 B1 | 3/2011 | | |
| EP | 2298408 A2 | 3/2011 | | |
| EP | 2310088 B1 | 4/2011 | | |
| EP | 2318088 B1 | 5/2011 | | |
| EP | 2380625 A1 | 10/2011 | | |
| EP | 2383015 A1 | 11/2011 | | |
| EP | 2462982 A1 | 6/2012 | | |
| EP | 2468358 B1 | 6/2012 | | |
| EP | 2476458 B1 | 7/2012 | | |
| EP | 2478931 B1 | 7/2012 | | |
| EP | 2550992 B1 | 1/2013 | | |
| EP | 2462983 A1 | 6/2013 | | |
| EP | 2617396 A2 | 7/2013 | | |
| EP | 2617457 A2 | 7/2013 | | |
| EP | 2617460 A2 | 7/2013 | | |
| EP | 2667933 B1 | 12/2013 | | |
| EP | 2905051 A1 | 8/2015 | | |
| EP | 2907542 A1 | 8/2015 | | |
| EP | 2932998 A1 | 10/2015 | | |
| EP | 2965782 A1 | 1/2016 | | |
| EP | 3002035 A1 | 4/2016 | | |
| EP | 2211977 A1 | 6/2016 | | |
| WO | WO 96/40367 | 12/1996 | | |
| WO | WO 97/37720 | 10/1997 | | |
| WO | WO 97/49454 | 12/1997 | | |
| WO | WO 98/11942 | 3/1998 | | |
| WO | WO 98/24510 | 6/1998 | | |
| WO | WO 99/39769 | 8/1999 | | |
| WO | WO 99/62594 | 12/1999 | | |
| WO | WO 00/02212 | 1/2000 | | |
| WO | WO 00/24456 | 5/2000 | | |
| WO | WO 01/39830 | 6/2001 | | |
| WO | WO 01/78216 | 10/2001 | | |
| WO | WO 03/009749 | 2/2003 | | |
| WO | WO 03/061335 | 7/2003 | | |
| WO | WO 03/066153 | 8/2003 | | |
| WO | WO 03/099377 | 12/2003 | | |
| WO | WO 2004/002572 | 1/2004 | | |
| WO | WO 2004/008954 | 1/2004 | | |
| WO | WO 2004/028624 | 4/2004 | | |
| WO | WO2004/058322 A2 | 7/2004 | | |
| WO | WO 2004/064729 | 8/2004 | | |
| WO | WO 2004/103455 | 12/2004 | | |
| WO | WO 2004/110549 | 12/2004 | | |
| WO | WO 2004/110550 | 12/2004 | | |
| WO | WO 2005/011805 | 2/2005 | | |
| WO | WO 2007/037370 | 4/2005 | | |
| WO | WO 2005/077276 | 8/2005 | | |
| WO | WO 2005/082452 | 9/2005 | | |
| WO | WO 2006/093964 | 9/2006 | | |
| WO | WO 2006/132810 | 12/2006 | | |
| WO | WO 2007/035361 | 3/2007 | | |
| WO | WO 2007/035774 | 3/2007 | | |
| WO | WO 2007/081714 | 7/2007 | | |
| WO | WO 2007/090047 | 8/2007 | | |
| WO | WO 2007/092865 | 8/2007 | | |
| WO | WO 2007/098202 | 8/2007 | | |
| WO | WO 2007/120305 | 10/2007 | | |
| WO | WO 2007/149572 | 12/2007 | | |
| WO | WO 2008/005903 | 1/2008 | | |
| WO | WO 2008/014028 | 1/2008 | | |
| WO | WO 2008/016802 | 2/2008 | | |
| WO | WO 2008/039921 | 4/2008 | | |
| WO | WO 2008/042058 | 4/2008 | | |
| WO | WO 2008/048724 | 4/2008 | | |
| WO | WO 2008/079700 | 7/2008 | | |
| WO | WO 2008/076646 | 8/2008 | | |
| WO | WO 2009/032625 | 3/2009 | | |
| WO | WO 2009029977 A1 | * 3/2009 | ............ A61N 1/372 | |
| WO | WO 2008/048580 | 4/2009 | | |
| WO | WO 2009/046044 | 4/2009 | | |
| WO | WO 2009/048580 | 4/2009 | | |
| WO | WO 2009/051536 | 4/2009 | | |
| WO | WO 2009/051538 | 4/2009 | | |
| WO | WO 2009/051539 | 4/2009 | | |
| WO | WO 2009/061537 | 5/2009 | | |
| WO | WO 2009/070086 | 6/2009 | | |
| WO | WO 2009/111012 | 9/2009 | | |
| WO | WO 2009/126354 | 10/2009 | | |
| WO | WO 2009/140636 | 11/2009 | | |
| WO | WO 2010/003106 | 1/2010 | | |
| WO | WO 2010/039853 | 4/2010 | | |
| WO | WO 2010/042020 | 4/2010 | | |
| WO | WO 2010/042404 | 4/2010 | | |
| WO | WO 2010/096776 | 8/2010 | | |
| WO | WO 2011/060056 | 5/2011 | | |
| WO | WO 2011/139779 | 11/2011 | | |

(56) References Cited

FOREIGN PATENT DOCUMENTS

| | | |
|---|---|---|
| WO | WO 2011/143490 | 11/2011 |
| WO | WO 2012/030522 | 3/2012 |
| WO | WO 2012/055389 | 5/2012 |
| WO | WO 2013/067538 | 5/2013 |
| WO | WO 2013/078092 | 5/2013 |
| WO | WO 2013/086212 | 6/2013 |
| WO | WO 2013/147799 | 10/2013 |
| WO | WO 2013/173214 | 11/2013 |
| WO | WO 2013/188400 | 12/2013 |
| WO | WO 2014/004526 | 1/2014 |
| WO | WO 2014/179685 | 11/2014 |

* cited by examiner

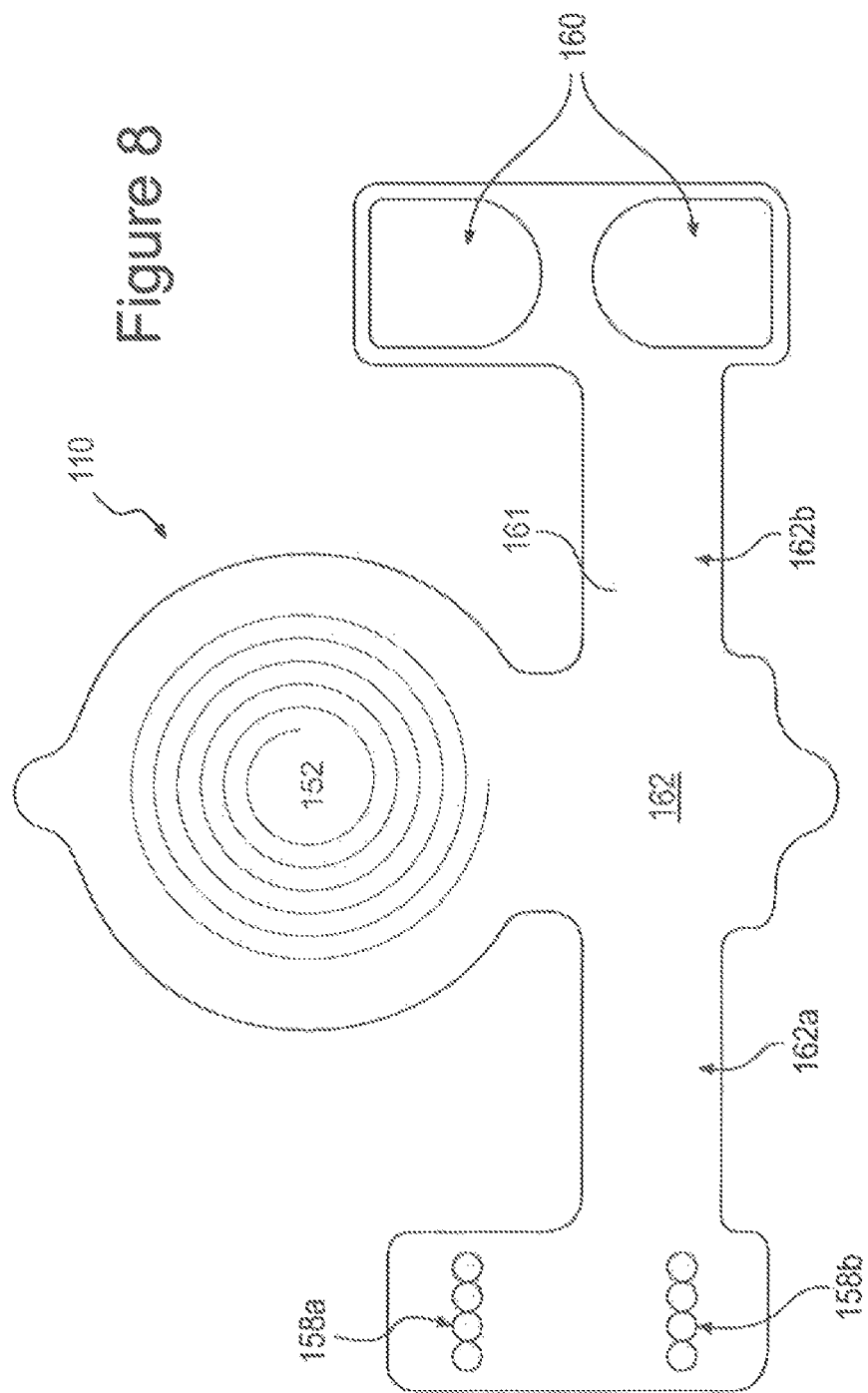

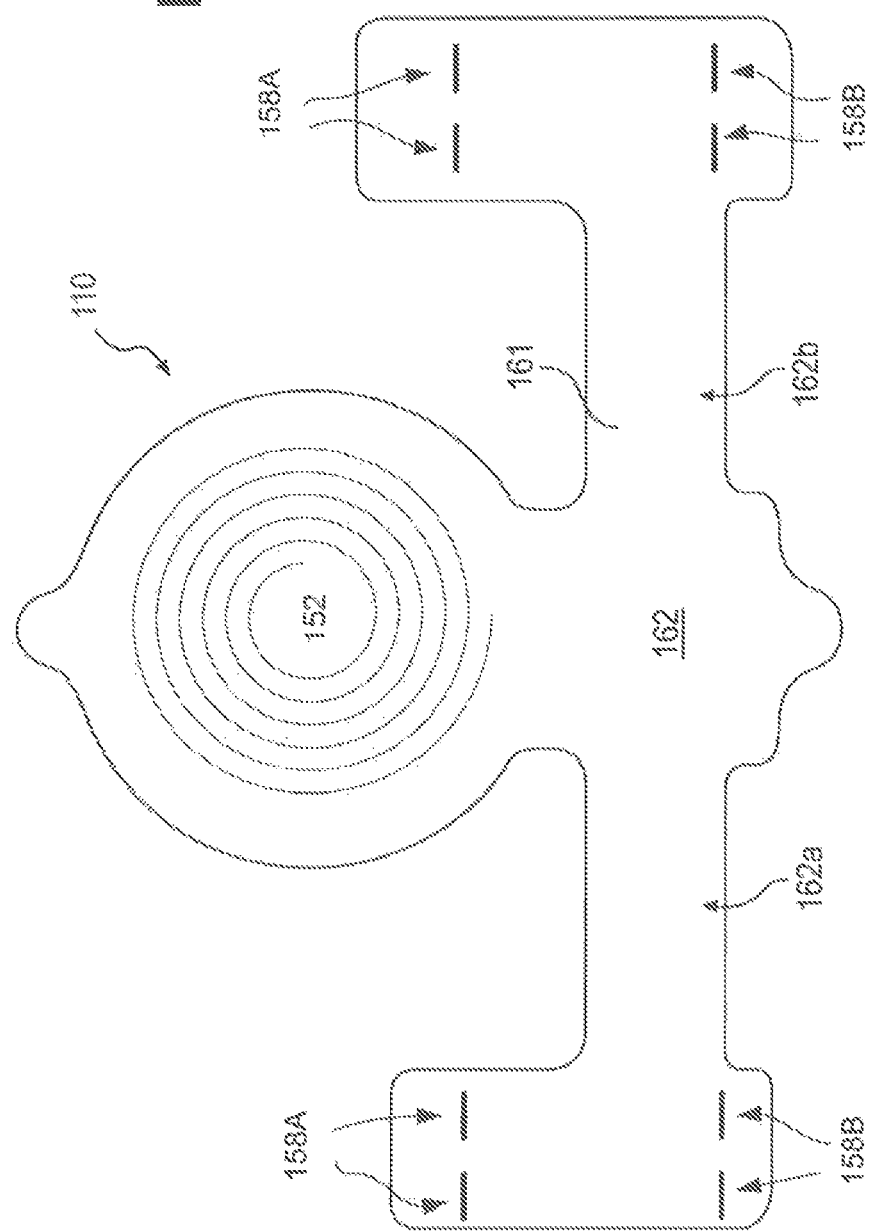

TRANSCUTANEOUS POWER CONVEYANCE DEVICE

RELATED APPLICATIONS

This application claims the benefit of priority under 35 U.S.C. §119(e) to U.S. Provisional Application No. 61/676,327, filed Jul. 26, 2012, which is incorporated herein by reference.

TECHNICAL FIELD

Embodiments of the present disclosure generally relate to devices and methods for conveying power from a location external to a subject to a location within the subject. More particularly, embodiments of the present disclosure relate to devices and methods for transcutaneously conveying power to an implanted neuromodulation device.

BACKGROUND

Neural modulation presents the opportunity to treat many physiological conditions and disorders by interacting with the body's own natural neural processes. Neural modulation includes inhibition (e.g. blockage), stimulation, modification, regulation, or therapeutic alteration of activity, electrical or chemical, in the central, peripheral, or autonomic nervous system. By modulating the activity of the nervous system, for example through the stimulation of nerves or the blockage of nerve signals, several different goals may be achieved. Motor neurons may be stimulated at appropriate times to cause muscle contractions. Sensory neurons may be blocked, for instance to relieve pain, or stimulated, for instance to provide a signal to a subject. In other examples, modulation of the autonomic nervous system may be used to adjust various involuntary physiological parameters, such as heart rate and blood pressure. Neural modulation may provide the opportunity to treat several diseases or physiological conditions, a few examples of which are described in detail below.

Among the conditions to which neural modulation may be applied is sleep disordered breathing, examples of which include obstructive sleep apnea (OSA) and snoring. OSA is a respiratory disorder characterized by recurrent episodes of partial or complete obstruction of the upper airway during sleep. During the sleep of a person without OSA, the pharyngeal muscles relax during sleep and gradually collapse, narrowing the airway. The airway narrowing limits the effectiveness of the sleeper's breathing, causing a rise in $CO_2$ levels in the blood. The increase in $CO_2$ results in the pharyngeal muscles contracting to open the airway to restore proper breathing. The largest of the pharyngeal muscles responsible for upper airway dilation is the genioglossus muscle, which is one of several different muscles in the tongue. The genioglossus muscle is responsible for forward tongue movement and the stiffening of the anterior pharyngeal wall. In patients with OSA, the neuromuscular activity of the genioglossus muscle is decreased compared to normal individuals, accounting for insufficient response and contraction to open the airway as compared to a normal individual. This lack of response contributes to a partial or total airway obstruction, which significantly limits the effectiveness of the sleeper's breathing. In OSA patients, there are often several airway obstruction events during the night. Because of the obstruction, there is a gradual decrease of oxygen levels in the blood (hypoxemia). Hypoxemia leads to night time arousals, which may be registered by EEG, showing that the brain awakes from any stage of sleep to a short arousal. During the arousal, there is a conscious breath or gasp, which resolves the airway obstruction. An increase in sympathetic tone activity rate through the release of hormones such as epinephrine and noradrenaline also often occurs as a response to hypoxemia. As a result of the increase in sympathetic tone, the heart enlarges in an attempt to pump more blood and increase the blood pressure and heart rate, further arousing the patient. After the resolution of the apnea event, as the patient returns to sleep, the airway collapses again, leading to further arousals.

These repeated arousals, combined with repeated hypoxemia, leaves the patient sleep deprived, which leads to daytime somnolence and worsens cognitive function. This cycle can repeat itself up to hundreds of times per night in severe patients. Thus, the repeated fluctuations in and sympathetic tone and episodes of elevated blood pressure during the night evolve to high blood pressure through the entire day. Subsequently, high blood pressure and increased heart rate may cause other diseases.

Efforts for treating OSA include Continuous Positive Airway Pressure (CPAP) treatment, which requires the patient to wear a mask through which air is blown into the nostrils to keep the airway open. Other treatment options include the implantation of rigid inserts in the soft palate to provide structural support, tracheotomies, or tissue ablation.

Another condition to which neural modulation may be applied is the occurrence of migraine headaches. Pain sensation in the head is transmitted to the brain via the occipital nerve, specifically the greater occipital nerve, and the trigeminal nerve. When a subject experiences head pain, such as during a migraine headache, the inhibition of these nerves may serve to decrease or eliminate the sensation of pain.

Neural modulation may also be applied to hypertension. Blood pressure in the body is controlled via multiple feedback mechanisms. For example, baroreceptors in the carotid body in the carotid artery are sensitive to blood pressure changes within the carotid artery. The baroreceptors generate signals that are conducted to the brain via the glossopharyngeal nerve when blood pressure rises, signaling the brain to activate the body's regulation system to lower blood pressure, e.g. through changes to heart rate, and vasodilation/vasoconstriction. Conversely, parasympathetic nerve fibers on and around the renal arteries generate signals that are carried to the kidneys to initiate actions, such as salt retention and the release of angiotensin, which raise blood pressure. Modulating these nerves may provide the ability to exert some external control over blood pressure.

The foregoing are just a few examples of conditions to which neuromodulation may be of benefit, however embodiments of the invention described hereafter are not necessarily limited to treating only the above-described conditions.

SUMMARY

Some embodiments of the present disclosure may include a device for conveying power from a location external to a subject to a location within the subject The device may include a flexible carrier, an adhesive on a first side of the carrier, a coil of electrically conductive material associated with the flexible carrier, and a mechanical connector extending from a second side of the carrier opposite the adhesive. The mechanical connector may be configured to be received by and retained by a receiver associated with a housing configured for mounting on the carrier.

In another embodiment, a device for connection to a flexible adhesive patch configured to convey power from a location external to a subject to a location within the subject, wherein the flexible adhesive patch includes adhesive on one side thereof and a protrusion extending from a side thereof opposite the adhesive may be provided. The device may include a housing configured to contain at least one processor, and a concavity within the housing. The concavity may be configured to receive and retain the protrusion extending from the flexible adhesive patch, and at least a portion of a side of the housing and a top of the housing may be exposed when the housing is mounted on the flexible adhesive patch.

In another embodiment, a device for connection to a flexible adhesive patch configured to convey power from a location external to a subject to a location within the subject, wherein the flexible adhesive patch includes adhesive on one side thereof and a recessed portion on a side thereof opposite the adhesive may be provided. The device may include a housing configured to contain at least one processor, and a protrusion extending from the housing, the protrusion being configured to engage and be retained within the recessed portion of the flexible adhesive patch, wherein at least a portion of a side of the housing and a top of the housing are exposed when the housing is mounted on the flexible adhesive patch.

Additional features of the disclosure will be set forth in part in the description that follows, and in part will be obvious from the description, or may be learned by practice of the disclosed embodiments.

It is to be understood that both the foregoing general description and the following detailed description are exemplary and explanatory only, and are not restrictive of the invention, as claimed.

BRIEF DESCRIPTION OF THE DRAWINGS

The accompanying drawings, which are incorporated in and constitute a part of this specification, illustrate several embodiments of the disclosure and, together with the description, serve to explain the principles of the embodiments disclosed herein.

FIG. 8 is a top view of an implant unit, according to an exemplary embodiment of the present disclosure.

FIG. 9 is a top view of another embodiment of an implant unit, according to an exemplary embodiment of the present disclosure.

DESCRIPTION OF EXEMPLARY EMBODIMENTS

Reference will now be made in detail to exemplary embodiments of the present disclosure, examples of which are illustrated in the accompanying drawings. Wherever possible, the same reference numbers will be used throughout the drawings to refer to the same or like parts.

Embodiments of the present disclosure relate generally to a device for modulating a nerve through the delivery of energy. Nerve modulation, or neural modulation, includes inhibition (e.g. blockage), stimulation, modification, regulation, or therapeutic alteration of activity, electrical or chemical, in the central, peripheral, or autonomic nervous system. Nerve modulation may take the form of nerve stimulation, which may include providing energy to the nerve to create a voltage change sufficient for the nerve to activate, or propagate an electrical signal of its own. Nerve modulation may also take the form of nerve inhibition, which may including providing energy to the nerve sufficient to prevent the nerve from propagating electrical signals. Nerve inhibition may be performed through the constant application of energy, and may also be performed through the application of enough energy to inhibit the function of the nerve for some time after the application. Other forms of neural modulation may modify the function of a nerve, causing a heightened or lessened degree of sensitivity. As referred to herein, modulation of a nerve may include modulation of an entire nerve and/or modulation of a portion of a nerve. For example, modulation of a motor neuron may be performed to affect only those portions of the neuron that are distal of the location to which energy is applied.

In patients with sleep disordered breathing, for example, a primary target response of nerve stimulation may include contraction of a tongue muscle (e.g., the muscle) in order to move the tongue to a position that does not block the patient's airway. In the treatment of migraine headaches, nerve inhibition may be used to reduce or eliminate the sensation of pain. In the treatment of hypertension, neural modulation may be used to increase, decrease, eliminate or otherwise modify nerve signals generated by the body to regulate blood pressure.

While embodiments of the present disclosure may be disclosed for use in patients with specific conditions, the embodiments may be used in conjunction with any patient/portion of a body where nerve modulation may be desired. That is, in addition to use in patients with sleep disordered breathing, migraine headaches, or hypertension, embodiments of the present disclosure may be use in many other areas, including, but not limited to: deep brain stimulation (e.g., treatment of epilepsy, Parkinson's, and depression); cardiac pace-making, stomach muscle stimulation (e.g., treatment of obesity), back pain, incontinence, menstrual pain, and/or any other condition that may be affected by neural modulation.

Figure 1:
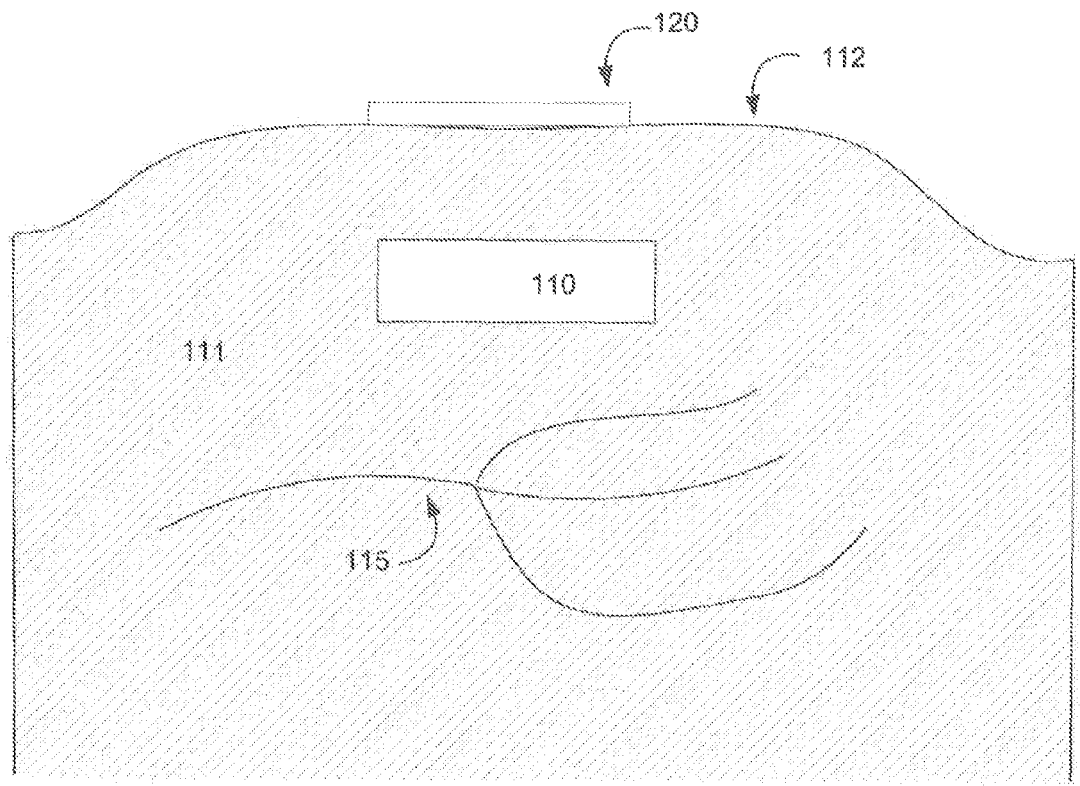
FIG. 1 diagrammatically illustrates an implant unit and external unit, according to an exemplary embodiment of the present disclosure.

FIG. 1 illustrates an implant unit and external unit, according to an exemplary embodiment of the present disclosure. An implant unit 110, may be configured for implantation in a subject, in a location that permits it to modulate a nerve 115. The implant unit 110 may be located in a subject such that intervening tissue 111 exists between the implant unit 110 and the nerve 115. Intervening tissue may include muscle tissue, connective tissue, organ tissue, or any other type of biological tissue. Thus, location of implant unit 110 does not require contact with nerve 115 for effective neuromodulation. The implant unit 110 may also be located directly adjacent to nerve 115, such that no intervening tissue 111 exists.

In treating sleep disordered breathing, implant unit 110 may be located on a genioglossus muscle of a patient. Such a location is suitable for modulation of the hypoglossal nerve, branches of which run inside the genioglossus muscle. For example, implant 110 may be configured to modulate terminal fibers of the hypoglossal nerve from a location spaced apart from (e.g., not contacting) the terminal fibers. Implant unit 110 may also be configured for placement in other locations. For example, migraine treatment may require subcutaneous implantation in the back of the neck, near the hairline of a subject, or behind the ear of a subject, to modulate the greater occipital nerve and/or the trigeminal nerve. Treating hypertension may require the implantation of a neuromodulation implant intravascularly inside the renal artery or renal vein (to modulate the parasympathetic renal nerves), either unilaterally or bilaterally, inside the carotid artery or jugular vein (to modulate the glossopharyngeal nerve through the carotid baroreceptors). Alternatively or additionally, treating hypertension may require the implantation of a neuromodulation implant subcutaneously, behind the ear or in the neck, for example, to directly modulate the glossopharyngeal nerve.

External unit 120 may be configured for location external to a patient, either directly contacting, or close to the skin 112 of the patient. External unit 120 may be configured to be affixed to the patient, for example, by adhering to the skin 112 of the patient, or through a band or other device configured to hold external unit 120 in place. Adherence to the skin of external unit 120 may occur such that it is in the vicinity of the location of implant unit 110.

Figure 2:
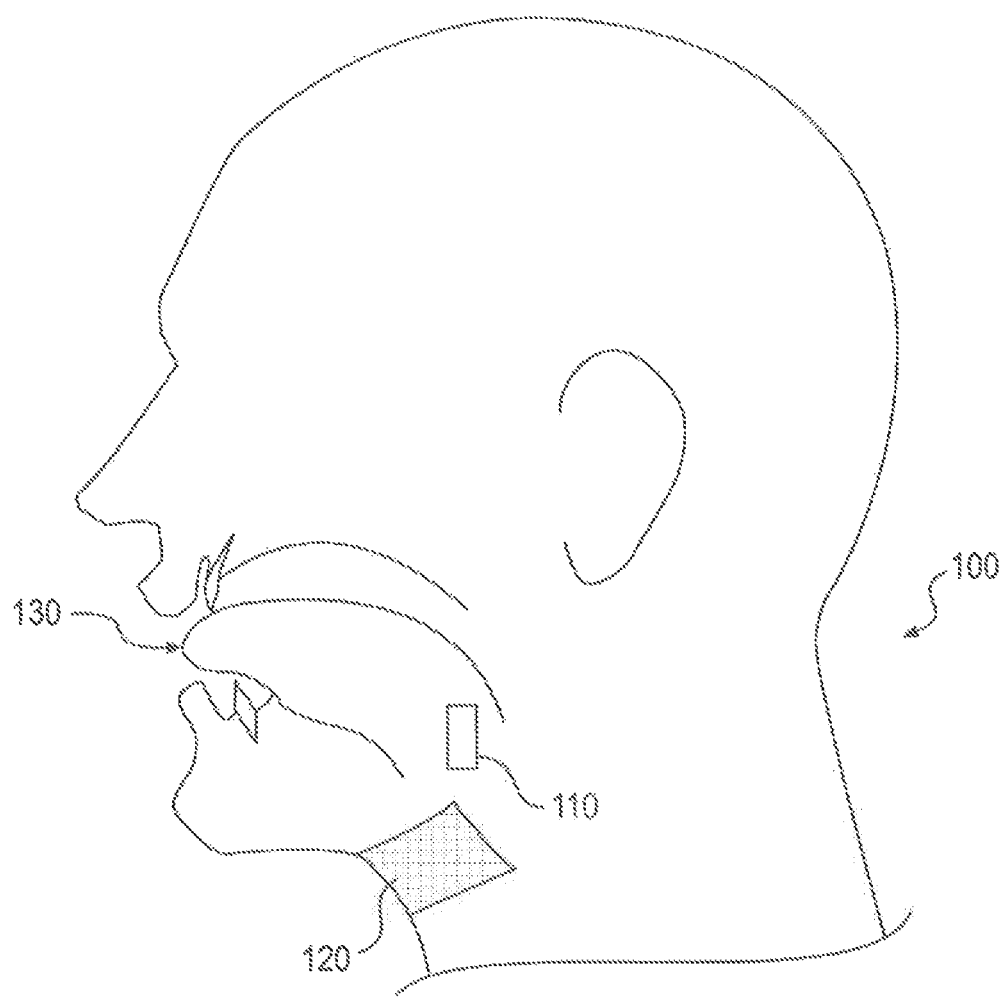
FIG. 2 is a partially cross-sectioned side view of a subject with an implant unit and external unit, according to an exemplary embodiment of the present disclosure.

FIG. 2 illustrates an exemplary embodiment of a neuromodulation system for delivering energy in a patient 100 with sleep disordered breathing. The system may include an external unit 120 that may be configured for location external to the patient. In some embodiments of the present disclosure, external unit 120 may include devices for conveying power from a location external to a subject to a location within a subject. For example, external unit 120 may include a carrier and an electronics housing, each configured as a portion of a system to convey power to implant unit 110, located within the subject.

As illustrated in FIG. 2, external unit 120 may be configured to be affixed to the patient 100. FIG. 2 illustrates that in a patient 100 with sleep disordered breathing, the external unit 120 may be configured for placement underneath the patient's chin and/or on the front of patient's neck. In some embodiments, external unit 120 may be positioned at a location on the patient's skin opposite to a location of terminal fibers of the hypoglossal nerve. The suitability of placement locations may be determined by communication between external unit 120 and implant unit 110, discussed in greater detail below. In alternate embodiments, for the treatment of conditions other than sleep disordered breathing, the external unit may be configured to be affixed anywhere suitable on a patient, such as the back of a patient's neck, i.e. for communication with a migraine treatment implant unit, on the outer portion of a patient's abdomen, i.e. for communication with a stomach modulating implant unit, on a patient's back, i.e. for communication with a renal artery modulating implant unit, and/or on any other suitable external location on a patient's skin, depending on the requirements of a particular application.

External unit 120 may further be configured to be affixed to an alternative location proximate to the patient. For example, in one embodiment, the external unit may be configured to fixedly or removably adhere to a strap or a band that may be configured to wrap around a part of a patient's body. Alternatively, or in addition, the external unit may be configured to remain in a desired location external to the patient's body without adhering to that location.

The external unit 120 may include a housing and a carrier. The housing may include any suitable container configured for retaining components. In addition, while the external unit is illustrated schematically in FIG. 2, the housing may be any suitable size and/or shape and may be rigid or flexible. Non-limiting examples of housings for the external unit 120 include one or more of patches, buttons, or other receptacles having varying shapes and dimensions and constructed of any suitable material. The carrier may include any type of substrate, rigid or flexible, to which the housing may be mounted. In one embodiment, for example, the carrier may include a flexible material such that external unit 120 may be configured to conform to a desired location. For example, as illustrated in FIG. 2, the carrier may include a skin patch, which, in turn, may include a flexible substrate. The material of the flexible substrate may include, but is not limited to, plastic, silicone, woven natural fibers, and other suitable polymers, copolymers, and combinations thereof. Any portion of external unit 120 may be flexible or rigid, depending on the requirements of a particular application.

As previously discussed, in some embodiments external unit 120 may be configured to adhere to a desired location. Accordingly, in some embodiments, at least one side of the carrier may include an adhesive material. The adhesive material may include a biocompatible material and may allow for a patient to adhere the external unit to the desired location and remove the external unit upon completion of use. The adhesive may be configured for single or multiple uses of the external unit. Suitable adhesive materials may include, but are not limited to biocompatible glues, starches, elastomers, thermoplastics, and emulsions.

Figure 3:
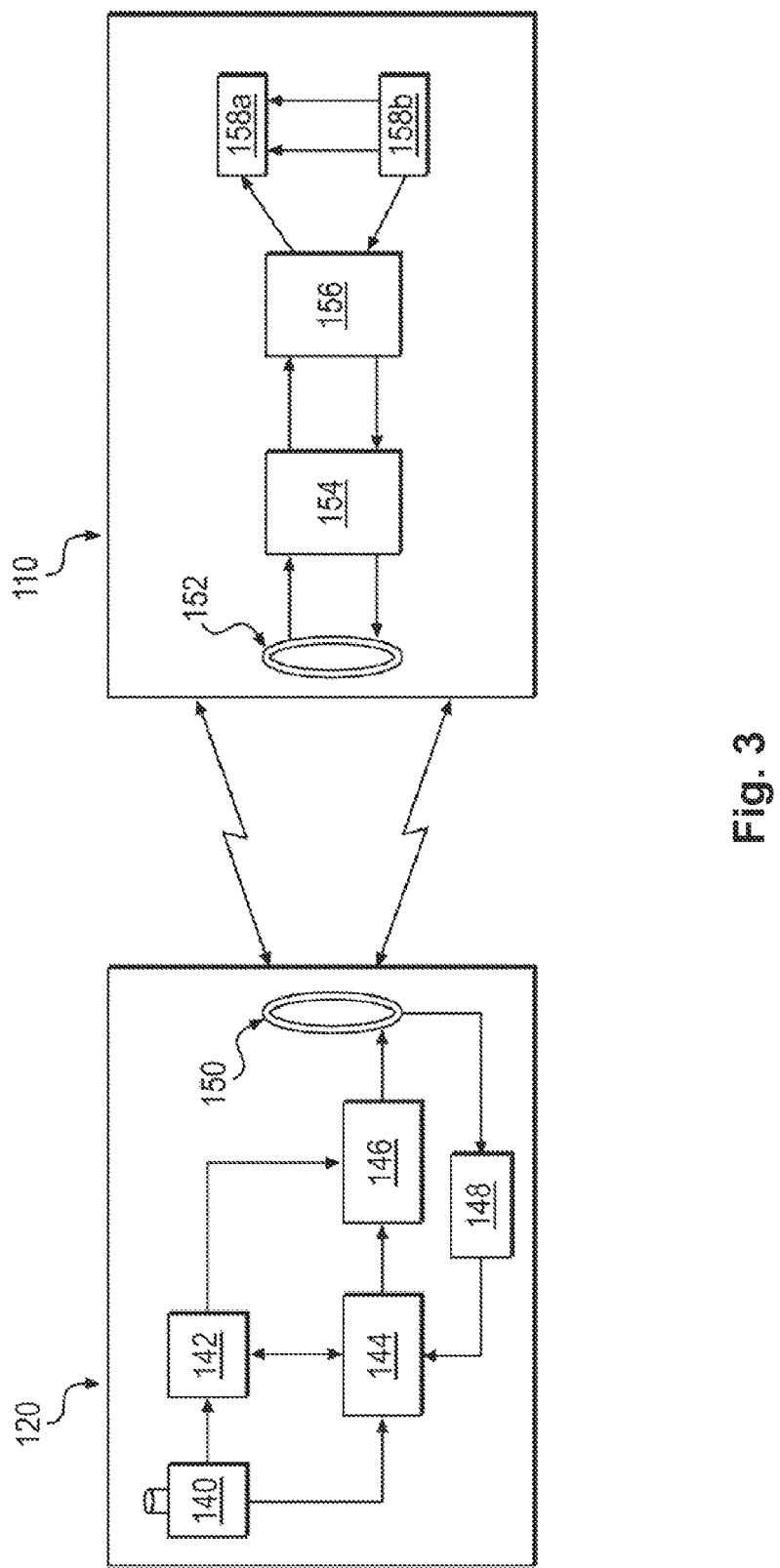
FIG. 3 diagrammatically illustrates a system including an implant unit and an external unit, according to an exemplary embodiment of the present disclosure.

FIG. 3 schematically illustrates a system including external unit 120 and an implant unit 110. In some embodiments, internal unit 110 may be configured as a unit to be implanted into the body of a patient, and external unit 120 may be configured to send signals to and/or receive signals from implant unit 110.

As shown in FIG. 3, various components may be included within a housing of external unit 120 or otherwise associated with external unit 120. As illustrated in FIG. 3, at least one processor 144 may be associated with external unit 120. For example, the at least one processor 144 may be located within the housing of external unit 120. In alternative embodiments, the at least one processor may be configured for wired or wireless communication with the external unit from a location external to the housing.

The at least one processor may include any electric circuit that may be configured to perform a logic operation on at least one input variable. The at least one processor may therefore include one or more integrated circuits, microchips, microcontrollers, and microprocessors, which may be all or part of a central processing unit (CPU), a digital signal processor (DSP), a field programmable gate array (FPGA), or any other circuit known to those skilled in the art that may be suitable for executing instructions or performing logic operations.

FIG. 3 illustrates that the external unit 120 may further be associated with a power source 140. The power source may be removably couplable to the external unit at an exterior location relative to external unit. Alternatively, as shown in FIG. 3, power source 140 may be permanently or removably coupled to a location within external unit 120. The power source may further include any suitable source of power configured to be in electrical communication with the processor. In one embodiment, for example the power source 140 may include a battery.

The power source may be configured to power various components within the external unit. As illustrated in FIG. 3, power source 140 may be configured to provide power to the processor 144. In addition, the power source 140 may be configured to provide power to a signal source 142. The signal source 142 may be in communication with the processor 144 and may include any device configured to generate a signal (e.g., a sinusoidal signal, square wave, triangle wave, microwave, radio-frequency (RF) signal, or any other type of electromagnetic signal). Signal source 142 may include, but is not limited to, a waveform generator that may be configured to generate alternating current (AC) signals and/or direct current (DC) signals. In one embodiment, for example, signal source 142 may be configured to generate an AC signal for transmission to one or more other components. Signal source 142 may be configured to generate a signal of any suitable frequency. In some embodiments, signal source 142 may be configured to generate a signal having a frequency of from about 6.5 MHz to about 13.6 MHz. In additional embodiments, signal source 142 may be configured to generate a signal having a frequency of from about 7.4 to about 8.8 MHz. In further embodiments, signal source 142 may generate a signal having a frequency as low as 90 kHz or as high as 28 MHz.

Signal source 142 may be configured for direct or indirect electrical communication with an amplifier 146. The amplifier may include any suitable device configured to amplify one or more signals generated from signal source 142. Amplifier 146 may include one or more of various types of amplification devices, including, for example, transistor based devices, operational amplifiers, RF amplifiers, power amplifiers, or any other type of device that can increase the gain associated one or more aspects of a signal. The amplifier may further be configured to output the amplified signals to one or more components within external unit 120.

The external unit may additionally include a primary antenna 150. The primary antenna may be configured as part of a circuit within external unit 120 and may be coupled either directly or indirectly to various components in external unit 120. For example, as shown in FIG. 3, primary antenna 150 may be configured for communication with the amplifier 146.

The primary antenna may include any electrically conductive material that may be configured to create an electromagnetic field. The primary antenna may further be of any suitable size, shape, and/or configuration. The size, shape, and/or configuration may be determined by the size of the patient, the placement location of the implant unit, the size and/or shape of the implant unit, the amount of energy required to modulate a nerve, a location of a nerve to be modulated, the type of receiving electronics present on the implant unit, etc. The primary antenna may include any suitable antenna known to those skilled in the art that may be configured to send and/or receive signals. Suitable antennas may include, but are not limited to, a long-wire antenna, a patch antenna, a helical antenna, etc. In one embodiment, for example, as illustrated in FIG. 3, primary antenna 150 may include a coil of electrically conductive material. Such a coil may be made from any suitable electrically conductive material and may be configured to include any suitable arrangement of conductive coils (e.g., diameter, number of coils, layout of coils, etc.). A coil antenna suitable for use as primary antenna 150 may have a diameter of between about 1 cm and 10 cm, and may be circular or oval shaped. In some embodiments, a coil antenna may have a diameter between 5 cm and 7 cm, and may be oval shaped. A coil antenna suitable for use as primary antenna 150 may have any number of windings, e.g. 4, 8, 12, or more. A coil antenna suitable for use as primary antenna 150 may have a wire diameter between about 0.01 mm and 2 mm. These antenna parameters are exemplary only, and may be adjusted above or below the ranges given to achieve suitable results.

As noted, implant unit 110 may be configured to be implanted in a patient's body (e.g., beneath the patient's skin). FIG. 2 illustrates that the implant unit 110 may be configured to be implanted for modulation of a nerve associated with a muscle of the subject's tongue 130. Modulating a nerve associated with a muscle of the subject's tongue 130 may include stimulation to cause a muscle contraction. In further embodiments, the implant unit may be configured to be placed in conjunction with any nerve that one may desire to modulate. For example, modulation of the occipital nerve, the greater occipital nerve, and/or the trigeminal nerve may be useful for treating pain sensation in the head, such as that from migraines. Modulation of parasympathetic nerve fibers on and around the renal arteries (i.e. the renal nerves), the vagus nerve, and/or the glossopharyngeal nerve may be useful for treating hypertension. Additionally, any nerve of the peripheral nervous system (both spinal and cranial), including motor neurons, sensory neurons, sympathetic neurons and parasympathetic neurons, may be modulated to achieve a desired effect.

Implant unit 110 may be formed of any materials suitable for implantation into the body of a patient. In some embodiments, implant unit 110 may include a flexible carrier 161 (FIG. 8) including a flexible, biocompatible material. Such materials may include, for example, silicone, polyimides, phenyltrimethoxysilane (PTMS), polymethyl methacrylate (PMMA), Parylene C, polyimide, liquid polyimide, laminated polyimide, black epoxy, polyether ether ketone (PEEK), Liquid Crystal Polymer (LCP), Kapton, etc. Implant unit 110 may further include circuitry including conductive materials, such as gold, platinum, titanium, or any other biocompatible conductive material or combination of materials. Implant unit 110 and flexible carrier 161 may also be fabricated with a thickness suitable for implantation under a patient's skin. Implant 110 may have thickness of less than about 4 mm or less than about 2 mm.

Other components that may be included in or otherwise associated with the implant unit are illustrated in FIG. 3. For example, implant unit 110 may include a secondary antenna 152 mounted onto or integrated with flexible carrier 161. Similar to the primary antenna, the secondary antenna may include any suitable antenna known to those skilled in the art that may be configured to send and/or receive signals. The secondary antenna may include any suitable size, shape, and/or configuration. The size, shape and/or configuration may be determined by the size of the patient, the placement location of the implant unit, the amount of energy required to modulate the nerve, etc. Suitable antennas may include, but are not limited to, a long-wire antenna, a patch antenna, a helical antenna, etc. In some embodiments, for example, secondary antenna 152 may include a coil antenna having a circular shape (see also FIG. 8) or oval shape. Such a coil antenna may be made from any suitable conductive material and may be configured to include any suitable arrangement of conductive coils (e.g., diameter, number of coils, layout of coils, etc.). A coil antenna suitable for use as secondary antenna 152 may have a diameter of between about 5 mm and 30 mm, and may be circular or oval shaped. A coil antenna suitable for use as secondary antenna 152 may have any number of windings, e.g. 4, 15, 20, 30, or 50. A coil antenna suitable for use as secondary antenna 152 may have a wire diameter between about 0.001 mm and 1 mm. These antenna parameters are exemplary only, and may be adjusted above or below the ranges given to achieve suitable results.

Figure 4:
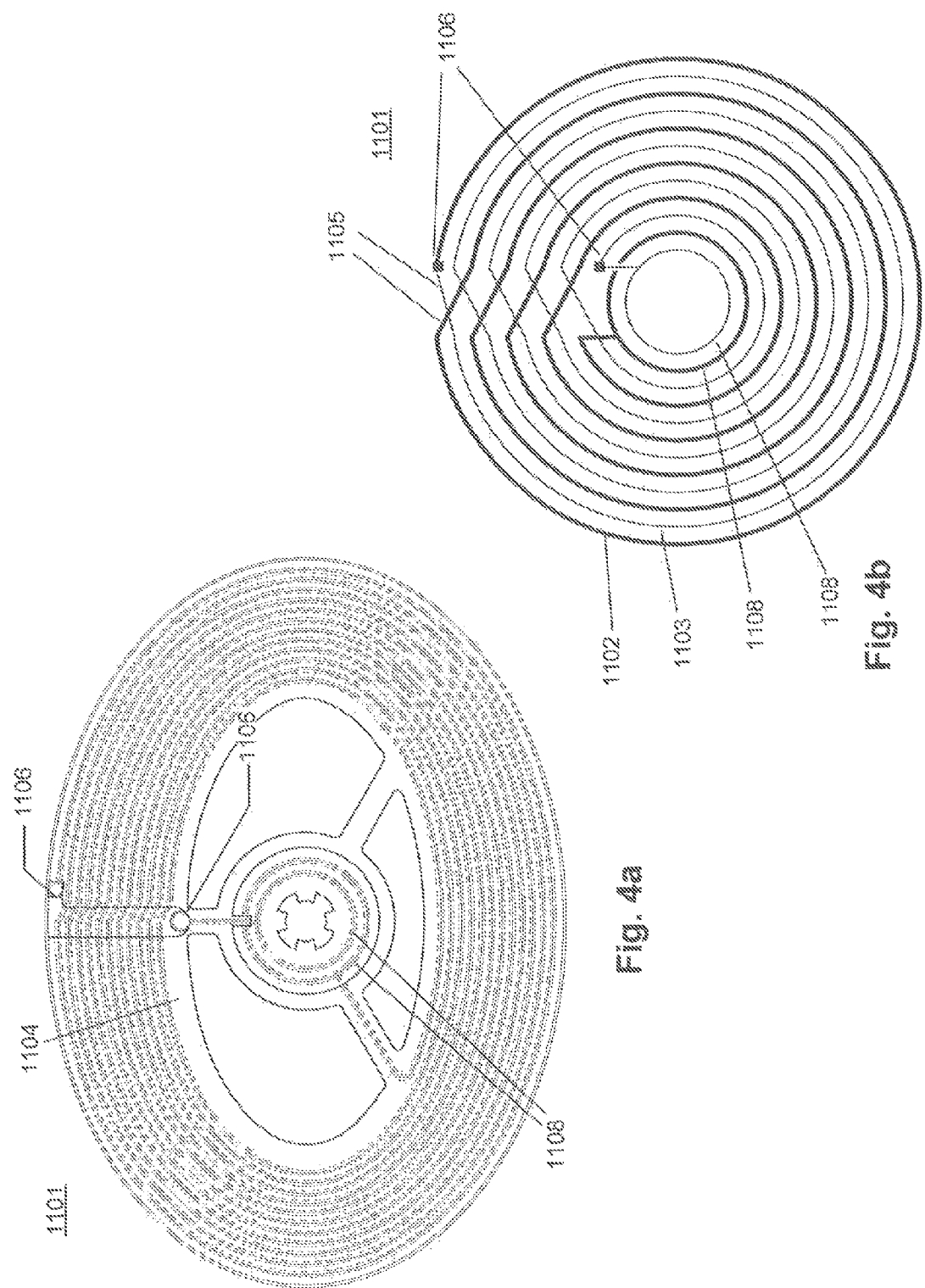
FIGS. 4a and 4b illustrate exemplary embodiments of a crossover antenna.

FIGS. 4a and 4b illustrate a double-layer crossover antenna 1101 suitable for use as a primary antenna 150. While the double-layer crossover antenna 1101 illustrated in FIGS. 4a and 4b includes features making it suitable for use as a primary antenna 150, some or all of the features of the double-layer crossover antenna, as described below, may also be utilized in a secondary antenna 152. While a double-layer crossover antenna is shown and described, other antenna configurations may also be suitable for primary antenna 150 and/or secondary antenna 152. For example, single layer antennas may be used where antenna components (e.g., coils) are arranged in a single layer, e.g., either on or within a dielectric or insulating material. Also, while a crossover pattern is shown, other patterns may also be suitable. For example, in some embodiments, a wire associated with primary antenna 150 and/or secondary antenna 152 may include a pattern of traces of progressively decreasing dimension. In the case of traces arranged in coils, for example, each loop could include rings of progressively decreasing diameter to create a pattern that spirals inwardly. A similar approach may be viable using traces of other shapes as well.

Returning to FIG. 4a, this figure illustrates a single coil of double-layer crossover antenna 1101, while FIG. 4b illustrates two layers of double layer crossover antenna 1101. Antenna 1101 may include a first coil of wire 1102 arranged on a first side of a dielectric carrier 1104 and a second coil of wire 1103 on a second side of a dielectric carrier 1104.

Arranging the antenna coils in a double layer may serve to increase the transmission range of the antenna without increasing the size of the antenna. Such an arrangement, however, may also serve to increase capacitance between the wires of each coil. In each wire coil, an amount of parasitic capacitance between wires may partially depend on the distance each wire is from its neighbor. In a single layer coil, capacitance may be generated between each loop of the coil and its neighbors to either side. Thus, more compact coils may generate more parasitic capacitance. When a second layer coil is added, additional capacitance may then be generated between the wires of the first coil and the wires of the second coil. This additional capacitance may be further increased if corresponding loops of the first and second coils have the same or similar diameters, and/or if a dielectric carrier separating the loops is made very thin. Increased parasitic capacitance in an antenna may serve to alter characteristics, such as resonant frequency, of the antenna in unpredictable amounts based on manufacturing specifications. Additionally, resonant frequency drift, caused, for example by moisture incursion or antenna flexing, may be increased by the presence of increased parasitic capacitance. Thus, in order to decrease variability in the manufactured product, it may be advantageous to reduce the levels of parasitic capacitance in a dual layer antenna.

FIG. 4b illustrates a double layer crossover antenna 1101 which may exhibit a parasitic capacitance in a manufactured antenna lower than single layer counterparts. As illustrated in FIG. 4b, a first coil of wire 1102 is concentrically offset from a second coil of wire 1103. In contrast to a configuration where each loop of a first coil 1102 has the same diameter as corresponding loop of the second coil 1103, concentrically offsetting corresponding loops of each wire coil serves to increase the distance between a single loop of the first coil 1102 with a corresponding loop of the second coil 1103. This increased distance, in turn, may decrease the parasitic wire-to-wire capacitance between loops of first coil 1102 and corresponding loops of second coil 1103. This configuration may be particularly advantageous in reducing parasitic capacitance in a situation where a dielectric carrier 1104 is thin enough such that the concentric distance by which each coil is offset is relatively large compared to the thickness of the dielectric carrier 1104. For example, in a situation where a dielectric carrier is 0.5 mm thick, a concentric offset of 0.5 mm or more may produce a large change in parasitic capacitance. In contrast, in a situation where a dielectric carrier is 5 mm thick, a concentric offset of 0.5 mm may produce a smaller change in parasitic capacitance. The concentric offset between a first coil 1102 and a second coil 1103 may be achieved, for example, by a plurality of electrical trace steps 1105 that offset each loop of the coils from each preceding loop. Electrical trace steps 1105 on a first side of dielectric carrier 1104 cross over electrical trace steps 1105 on a second side of dielectric carrier 1104, thus providing the crossover feature of double-layer crossover antenna 1101.

In additional embodiments, double layer crossover antenna 1101 may include openings 1106 in dielectric carrier 1104 to facilitate the electrical connection of first and second coils 1102, 1103. First and second coils 1102, 1103 of double layer crossover antenna 1101 may also include exposed electrical portions 1108, 1109 configured to electrically connect with an electrical connector of a device housing that may be coupled to antenna 1101. Exposed electrical portions 1108, 1109 may be configured so as to maintain electrical contact with the electrical connector of a device housing independent of the axial orientation of the connection. As shown in FIG. 4a, for example, exposed electrical portions 1108, 1109 may be configured as continuous or discontinuous circles in order to achieve this. A first exposed electrical portion 1108 configured as a discontinuous circle may provide a space through which an electrical trace may pass without contacting the first exposed electrical portion, for example to connect with a second exposed electrical portion 1109 located inside the first, or to other components located within the circle of the first exposed electrical portion 1108. FIG. 4a illustrates an antenna having substantially elliptical coils; other shapes, such as circular, triangular, square, etc., may be also be used in different embodiments. Elliptical coils may facilitate placement of external unit 120 in certain areas (e.g., under the chin of a subject) while maintaining desirable electrical performance characteristics.

Figure 5:
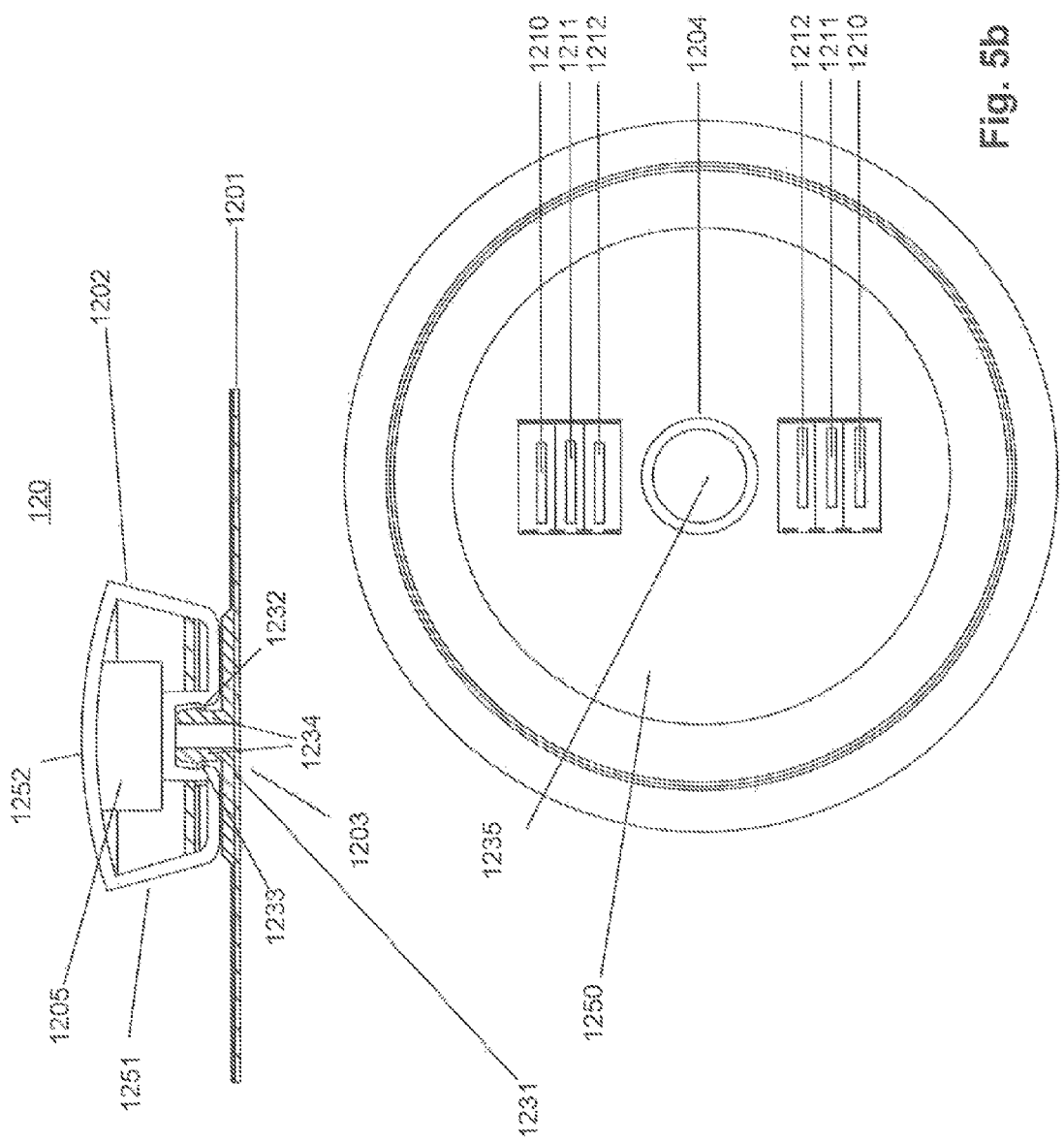
FIGS. 5a and 5b illustrate an exemplary embodiment of an external unit.

FIGS. 5a and 5b illustrate an exemplary embodiment of external unit 120, including features that may be found in any combination in other embodiments. FIG. 5a illustrates a side view of external unit 120, depicting carrier 1201 and electronics housing 1202.

Housing 1202 may be configured to contain various electrical and mechanical components, as further discussed below with respect to FIG. 5a. Housing 1202 may include a bottom surface 1250, a top surface 1252, and at least one sidewall 1251. When configured in a generally cylindrical arrangement, sidewall 1251 may include a continuous surface. Bottom surface 1250 may be configured to directly contact carrier 1201 or various contacts may be included on bottom surface 1250 to interact with carrier 1201.

Figure 6:
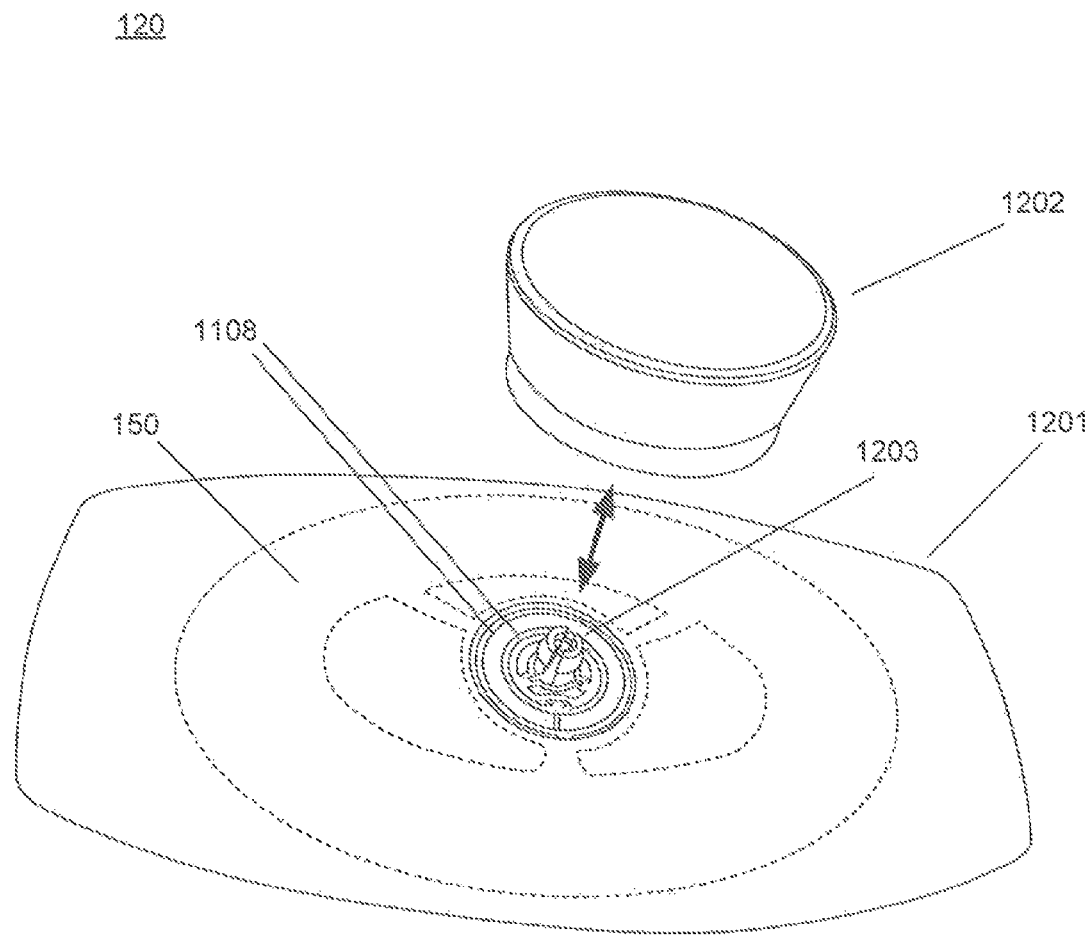
FIG. 6 is a perspective view of an exemplary external unit.

Carrier 1201 may include a skin patch configured for adherence to the skin of a subject, for example through adhesives of mechanical means. Carrier 1201 may be flexible or rigid, or may have flexible portions and rigid portions. In some embodiment, carrier 1201 may constitute a flexible adhesive patch. Carrier 1201 may be associated with a coil of electrically conductive material, for example, primary antenna 150. In some embodiments, (as illustrated in FIG. 6) primary antenna 150 may be located on or within carrier 1201. In some embodiments, carrier 1201 may include a double-layer crossover antenna 1101 such as the antennas illustrated in FIGS. 4a and 4b. Carrier 1201 may also include a power source 140, which may include a paper battery, thin film battery, or other type of substantially flat and/or flexible battery. Carrier 1201 may also include any other type of battery or power source.

Carrier 1201 may also include a connector 1203 configured for selectively or removably connecting carrier 1201 to electronics housing 1202. In some embodiments, connector 1203 may constitute a mechanical connector that includes at least one portion that extends away from carrier 1201. For example, connector 1203 may include a protrusion extending or protruding from carrier 1201. Connector 1203 may be configured to be received and retained by a receiver 1204 of electronics housing 1202. Retention of connector 1203 by receiver 1204 may be selective such that connector 1203 may be selectively removable from receiver 1204.

Connector 1203 may include various configurations. For example, connector 1203 may include a rodlike element 1231. Rodlike element 1231 may include any elongated structure of any cross-section. For example, rodlike element 1231 may be circular or oval in cross section, or may include a square or other-sided polygonal cross-section. Rodlike element 1231 may include a single integral protrusion, or may consist of several discrete protrusions grouped together to form rodlike element 1231. Such discrete portions may include flexible arms 1234. Connector 1203 may further include a detent portion 1232, for example, a notch or tab configured to engage with a corresponding detent engagement portion 1233 disposed on receiver 1204. Detent engagement portion may be, for example, a lip, rim, or flange. In some embodiments, detent portion 1232 may be disposed on flexible arms 1234, configured to elastically bend to permit engagement with receiver 1204 and return to their original positions to retain electronics housing 1202 in a mounted configuration. In some embodiments, connector 1203 may include a bayonet connector. In additional embodiments, connector 1203 may include a twist-lock connector. In some embodiments, connector 1203 may include various combinations of the above described retention features.

In further embodiments, connector 1203 may be configured to provide a selective connection to electronics housing 1204 without the substantial use of a concave feature into which at least a portion of housing 1202 is introduced in order to retain housing 1202 with carrier 1201. Connector 1203 may include, for example a peg, and may have flexible arms. Connector 1203 may further include a magnetic connection, a velcro connection, and/or a snap dome connection. Connector 1203 may also include a locating feature, configured to locate electronics housing 1202 at a specific height, axial location, and/or axial orientation with respect to carrier 1201. A locating feature of connector 1203 may further include pegs, rings, boxes, ellipses, bumps, etc. Connector 1203 may be centered on carrier 1201, may be offset from the center by a predetermined amount, or may be provided at any other suitable location of carrier 1201.

Multiple connectors 1203 may be provided on carrier 1201. Connector 1203 may be configured such that removal from electronics housing 1202 causes breakage of connector 1203. Such a feature may be desirable to prevent re-use of carrier 1201, which may lose some efficacy through continued use.

Receiver 1204 may also include various configurations to facilitate the retention of mechanical connector 1203. For example, in the embodiment illustrated in FIGS. 5a and 5b, receiver 1204 may include an opening into which mechanical connector 1203 extends. The opening may be a concavity 1235, configured to receive and retain connector 1203. The concavity may include a rim portion, extending around at least a portion of the perimeter of the interior of the cavity, and configured to engage a detent portion 1232 of connector 1203. Alternative embodiments or receiver 1204 and connector 1203 are described below with respect to FIGS. 7a-f.

As illustrated in FIG. 5a, when a user mounts housing 1202 to carrier 1201, housing 1202 may be retained by connector 1203 in a manner in which at least a portion of a sidewall 1251 and a top surface 1252 of the housing is exposed when mounted to the carrier. The exposure of a portion of a sidewall 1251 and a top surface 1252 of the housing may permit a user to easily grasp housing 1202, to facilitate mounting and/or removal from carrier 1201. In alternative embodiments, wherein housing 1202 is mounted to carrier 1201 via engagement with a receiver 1204 disposed at a perimeter of housing 1202, connector 1203 may engage with receiver 1204 at portions of the perimeter, thereby leaving at least top surface 1252 exposed.

Electronics housing 1202 is illustrated in side view in FIG. 5a and in a bottom view in FIG. 5b. Electronics housing 1202 may include electronics portion 1205, which may be arranged inside electronics housing 1202 in any manner that is suitable. Electronics portion 1205 may include various components, further discussed below, of external unit 120. For example, electronics portion 1205 may include any combination of at least one processor 144 associated with external unit 120, a power source 140, such as a battery, a primary antenna 152, and an electrical circuit 170. Electronics portion 1205 may also include any other component described herein as associated with external unit 120. Additional components may also be recognized by those of skill in the art.

Electronics housing 1202 may include receiver 1204 configured to receive and retain connector 1203. Electronics housing 1202 may include at least one electrical connector 1210, 1211, 1212. Electrical connectors 1210, 1211, 1212 may be arranged with pairs of electrical contacts, as shown in FIG. 5b, or with any other number of electrical contacts. The pair of electrical contacts of each electrical connector 1210, 1211, 1212 may be electrically connected with each other inside of housing 1202, such that the pair of electrical contacts represents a single connection point to a circuit. In such a configuration, it may only be necessary that one of the electrical contacts within a pair be contacted in order to establish a suitable electrical connection between electrical connectors 1210, 1211, 1212 and any corresponding connection elements provided on housing 1202, for example. Electrical connectors 1210, 1211, and 1212 may thus include redundant electrical contacts. The electrical contacts of each electrical connector 1210, 1211, 1212 may also represent opposite ends of a circuit, for example, the positive and negative ends of a battery charging circuit. In an exemplary embodiment, as shown in FIG. 5b, mechanical connector 1203 may be configured to maintain contact between electrical connectors 1210, 1211, and 1212, arranged on bottom surface 1250 of housing 1202 and exposed electrical portions 1108, 1109 (FIG. 6) of carrier 1201 when mechanical connector 1203 is received by receiver 1204 of electronics housing 1202.

As illustrated in FIGS. 5a and 5b, mechanical connector 1203 may be adapted to permit relative rotation between carrier 1201 and housing 1202. For example, in an embodiment wherein mechanical connector 1203 includes substantially circular extension, housing 1202 may include a spin on connector 1203, permitting relative rotation between carrier 1201 and housing 1202. In alternative examples, wherein mechanical connector 1203 engages with receiver 1204 disposed on a perimeter of housing 1202, housing 1202 may be permitted to rotate within a circular portion defined by mechanical connector 1203.

In embodiments permitting relative rotation between carrier 1201 and housing 1202, electrical connectors 1210, 1211, and 1212 may be configured so as to maintain electrical contact with an exposed electrical portions 1108, 1109 independent of an axial orientation of electronics housing 1202. Connection between any or all of electrical connectors 1210, 1211, 1212 and exposed electrical portions 1108, 1109 may thus be established and maintained irrespective of relative axial positions of carrier 1201 and housing 1202. Thus, when connector 1203 is received by receiver 1204, housing 1202 may rotate with respect to carrier 1201 without interrupting electrical contact between at least one of electrical connectors 1210, 1211, 1212 and exposed electrical portions 1108, 1109. Axial orientation independence may be achieved, for example, through the use of circular exposed electrical portions 1108, 1109 and each of a pair of contact portions 1213 of electrical connectors 1210, 1211, 1212 disposed equidistant from a center of receiver 1204 at a radius approximately equal to that of a corresponding exposed first electrical portion 1108. In this fashion, even if exposed electrical portion 1108 includes a discontinuous circle, at least one electrical contact 1213 of electrical connectors 1210, 1211, and 1212 may make contact with a corresponding first electrical portion 1108. In FIG. 5b, electrical connectors 1210, 1211, 1212 are illustrated as pairs of rectangular electrical contacts. Electrical connectors 1210, 1211, 1212, however, may include any number of contacts 1213, be configured as continuous or discontinuous circles, or have any other suitable shape or configuration.

One exemplary embodiment may operate as follows. As shown in FIG. 5b, electronics housing 1202 may include more electrical connectors 1210, 1211, 1212, than a carrier 1201 includes exposed electrical portions 1108. In the illustrated embodiments, electronics housing 1202 includes three electrical connectors 1210, 1211, and 1212, while a double-layer crossover antenna 1101 includes two exposed electrical portions 1108. Other configurations, however, are possible without departing from the scope of the invention. In the illustrated embodiment, each of connectors 1210, 1211, and 1212 includes two electrical contact portions 1213. In alternate embodiments, connectors 1210, 1211, and 1212 may include fewer or more than two electrical contact portions. The multiple electrical contact portions 1213 of an individual electrical connector 1210, 1211, or 1212 are in continuous electrical communication with each other, such that there is minimal electrical resistance between the multiple contact portions 1213 or each individual connector.

In the present embodiment, two of electrical connectors 1210, 1211, and 1212, for example 1211 and 1212 may each be configured with two electrical contact portions 1213. Electrical connectors 1211 and 1212 may be arranged such that connector 1211, through its contact portions 1213, makes contact with first exposed electrical portion 1108 and connector 1210, through its contact portions 1213, makes contact with second exposed electrical portion 1109. Exposed electrical portions 1108 and 1109 represent opposite ends of double layer crossover antenna 1101. Thus, antenna 1101 may be electrically connected to the electrical components contained in electronics portion 1205.

When connected to carrier 1201 in this configuration, contact portions 1213 of electrical connector 1210 may be configured so as not to contact either of exposed electrical portions 1108, 1109. In this embodiment, electrical connector 1210 may be reserved to function as opposite ends of a battery charging circuit, in order to charge a battery contained in electronics portion 1205 when electronics housing 1202 is not being used for therapy. A battery charger unit may be provided with a connector similar to that of connector 1203, and configured to engage with receiver 1204. Upon engaging with receiver 1204, electrode contacts of the battery charger unit may contact electrical contact portions 1213 of connector 1210 to charge a battery contained within electronics portion 1205.

In an additional embodiment consistent with the present disclosure, an activator chip may include electronics housing 1202. Processor 144 may be configured to activate when at least one of electrical connectors 1210, 1211, 1212 contact exposed electrical portions 1108, 1109 included in carrier 1201. In this manner, an electronics housing 1202 may be charged and left dormant for an extended period of time (e.g., one or more days) prior to activation. Simply connecting electronics housing 1202 to carrier 1201 (and inducing contact between an electrical connector 1210, 1211, 1212 and an electrical portion 1108, 1109) may cause the processor to activate. Upon activation, processor 144 may be configured to enter a specific mode of operation, such as a calibration mode (for calibrating the processor after placement of the carrier on the skin), a placement mode (for assisting a user to properly place the carrier on the skin), and/or a therapy mode (to begin a therapy session). The various modes of processor 144 may include waiting periods at the beginning, end, or at any time during. For example, a placement mode may include a waiting period at the end of the mode to provide a period during which a subject may fall asleep. A therapy mode may include a similar waiting period at the beginning of the mode. Additionally or alternatively, processor 144 may be configured to provide waiting periods separate from the described modes, in order to provide a desired temporal spacing between system activities.

FIG. 6 provides a perspective view of an exemplary external unit 120. As illustrated in FIG. 6, carrier 1201 may include a connector 1203 extending from carrier 1201. Connector 1203 may be configured to be received and retained by a receiver associated with housing 1202. For example, connector 1203 may be configured as a peg, post, tab (or any of the structures described above relative to connector 1203) shaped to be received into one or more recessed areas associated with housing 1202. Similarly, connector 1203 and/or housing 1202 may include structures (e.g., detents, etc.) to enable selective attachment to and retention of connector 1203 by housing 1202. In this way, housing 1202 may be mounted on carrier 1201. Once mounted, the electrical connectors 1210, 1211, 1212 of housing 1202 may engage with exposed electrical portions 1108, 1109 of carrier 1201.

Figure 7A:
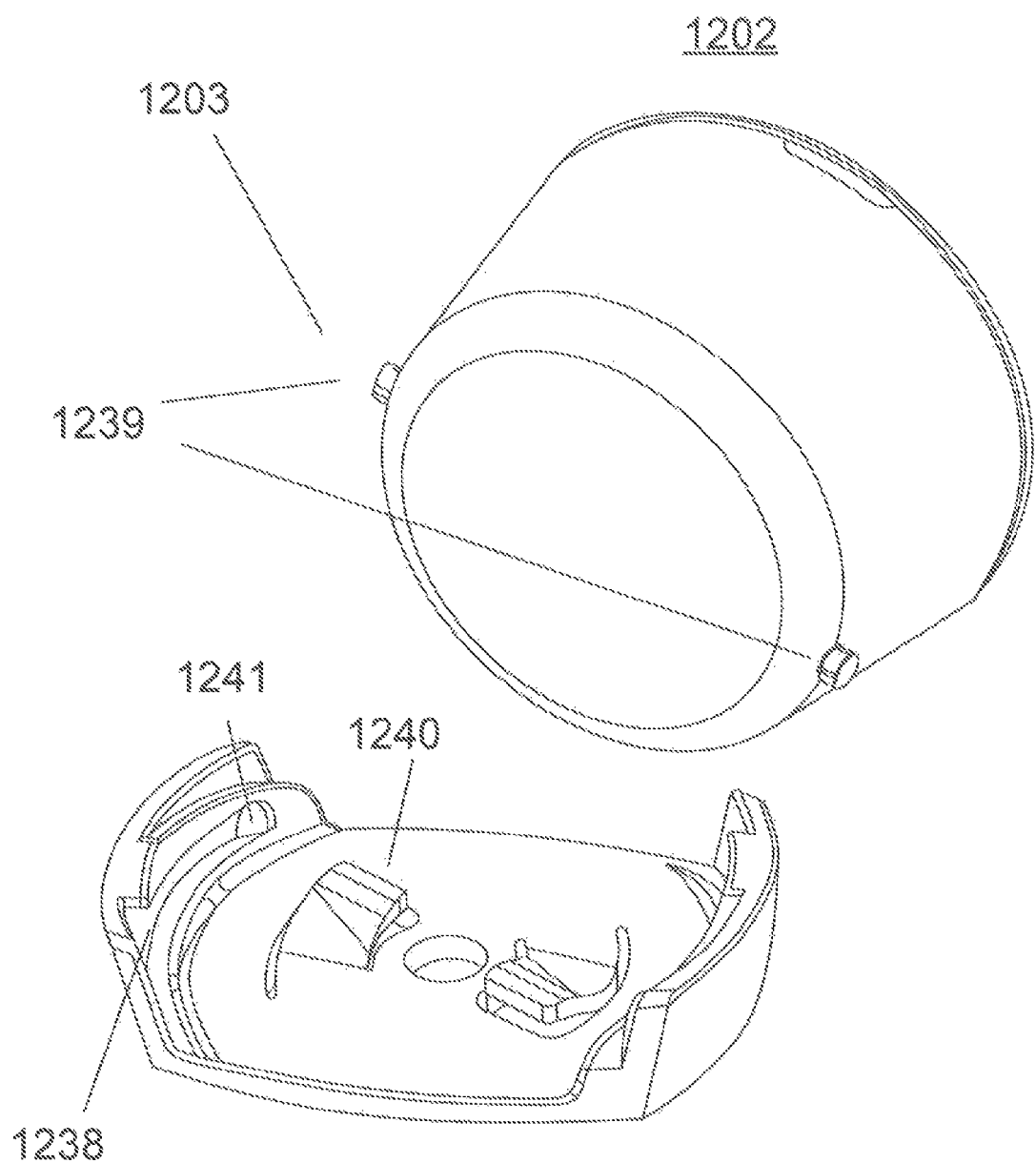
FIGS. 7a-7f illustrate exemplary embodiments of an external unit.

FIGS. 7a-f illustrate several additional exemplary embodiments of structures for enabling selective mounting of housing 1202 to carrier 1201. For example, FIG. 7a illustrates an exemplary embodiment of an external unit featuring a bayonet mount. In this embodiment connector 1203 may include extending portions 1218 configured to extend or protrude from carrier 1201. Extending portions 1218 may include receptor slots 1238 and retaining portions 1241. Further, connector 1203 may include at least one biasing mechanism 1240 configured to extend or protrude from the carrier. Receiver 1203 may include a plurality of radial pins 1239, corresponding in number to receptor slots 1238. Radial pins 1239 may be disposed on a portion of a perimeter of the housing. Carrier 1201 is not illustrated in FIG. 7a; however, connector 1203 may form part of carrier 1201, for example, as an integrally formed portion or as a portion affixed to carrier 1201. Radial pins 1239 may be configured as protrusions extending from the housing, and may be configured to engage and retain receptor slots 1238 of connector 1203. Radial pins 1239 may further be configured to be inserted into the receptor slots 1238 and to securely engage connector 1203 when the housing 1202 is rotated with respect to connector 1203. Although FIG. 7a illustrates an embodiment including two radial pins 1239, any suitable number of radial pins 1239 may be included. Biasing mechanism 1240 may provide a vertical force to seat radial pins 1239 in retention portion 1241 of receptor slot 1238. Biasing mechanism 1240 may include any type of elastically deformable element capable of providing a biasing force. For example, biasing mechanism may include a spring, or may include flexible plastic tabs. In some embodiments, biasing mechanism 1240 and electrical connectors 1210, 1211, and 1212 may be incorporated in the same structure. For example, electrical connectors 1210, 1211, and 1212 may include elastically deformable metal tabs configured to act as biasing mechanism 1240 by providing a biasing force. Biasing mechanism 1240 may be provided on as part of connector 1203 (as illustrated) or, in some embodiments, as part of receiver 1204 on housing 1202.

Figure 7B:
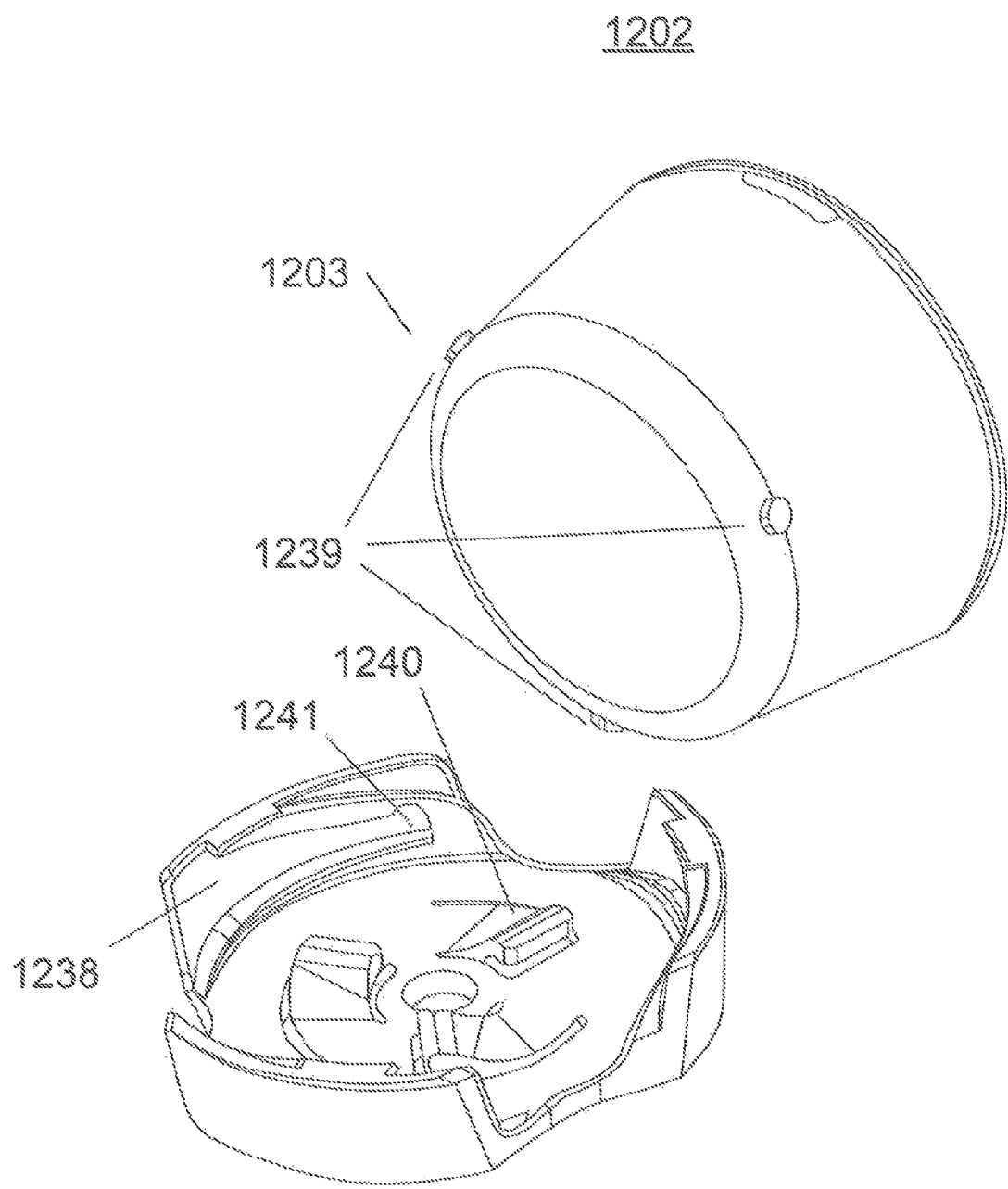

FIG. 7b illustrates an additional embodiment including a bayonet mount. FIG. 7b illustrates a bayonet mount including three radial pins 1239. Carrier 1201 is not illustrated in FIG. 7b; however, connector 1203 may form part of carrier 1201, for example, as an integrally formed portion or as a portion affixed to carrier 1201.

Figure 7C:
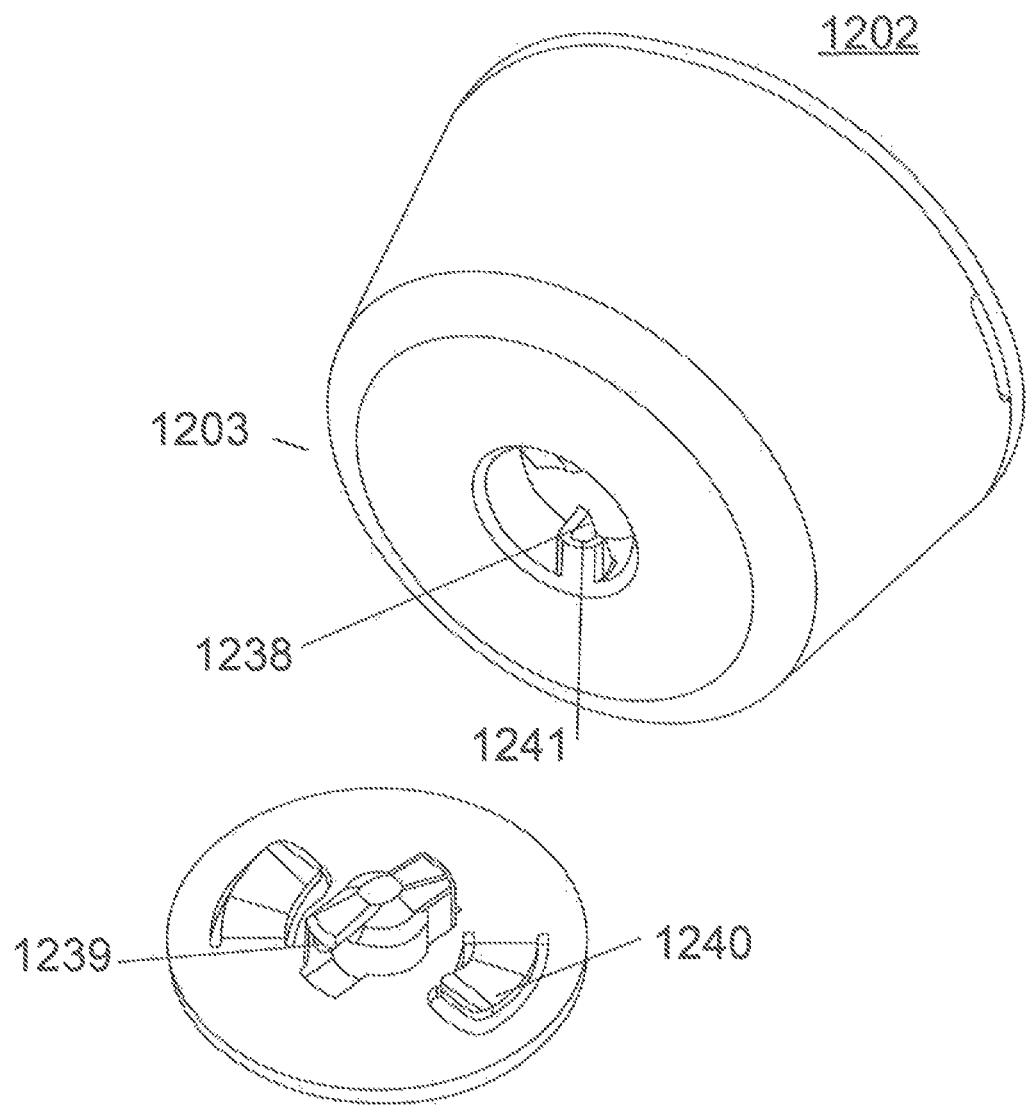

FIG. 7c illustrate an additional embodiment including a bayonet mount. For clarity purposes, carrier 1201 is not illustrated in FIG. 7c. Connector 1203 may include an extending portion 1218 and biasing mechanisms 1240 configured to extend or protrude from carrier 1201. As illustrated in FIG. 7c, protruding connector 1203 may include radial pins 1239 for bayonet mounting, and may be arranged inside of a perimeter provided by biasing mechanism 1240. Receiver 1204 may include a recessed portion including receptor slot 1238 and retention portions 1241. Connector 1203 may be configured to engage and be retained by receiver 1204 by inserting extending portion 1218 into the recessed portion of receiver 1204 and rotating housing 1202 with respect to connector 1203. During rotation, biasing mechanisms 1240 may be compressed. When radial pins 1239 are seated in retention portions 1241, biasing mechanisms 1240 may press housing 1202 away from carrier 1201, thus preventing further rotation between the two.

Figure 7D:
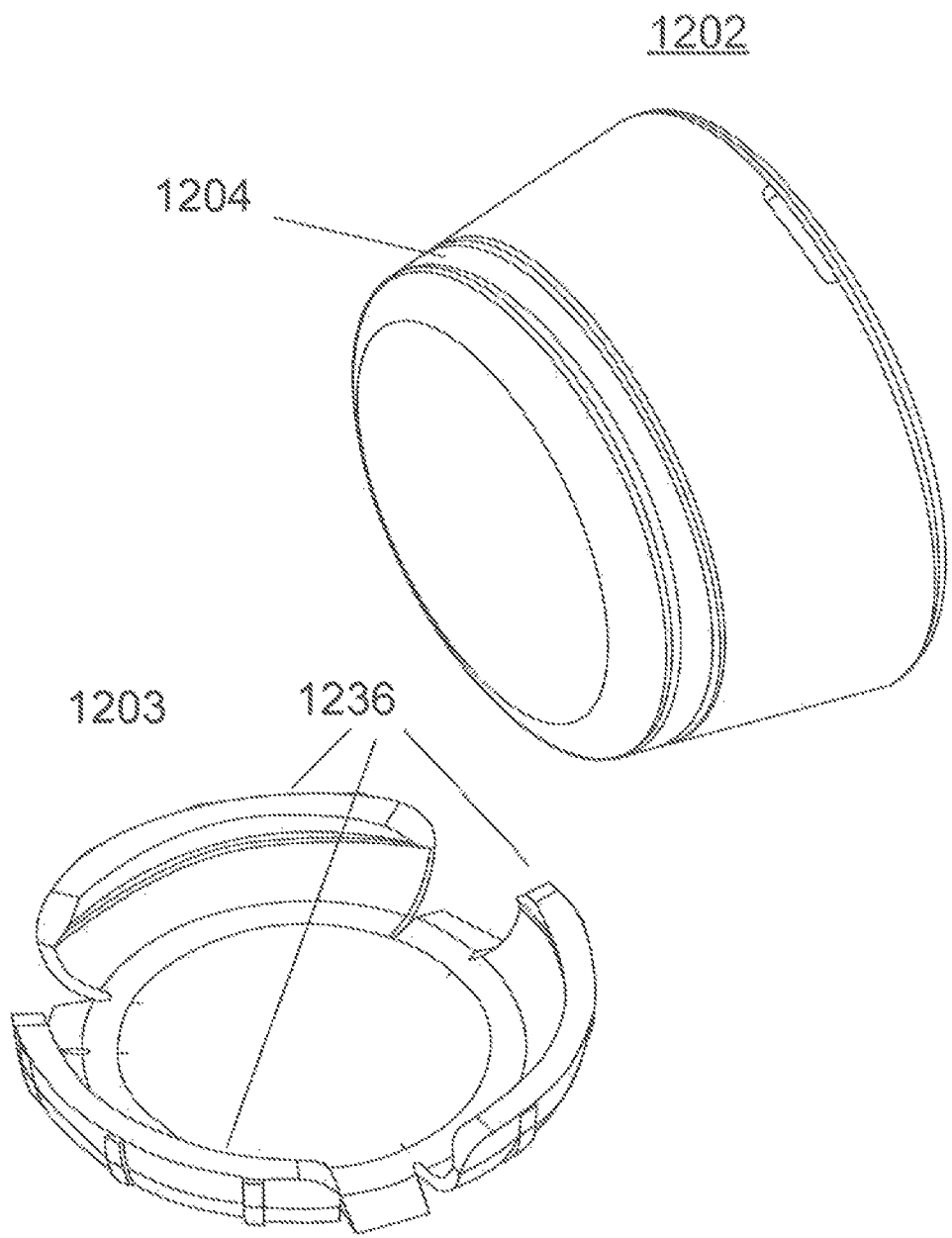

FIG. 7d illustrates an embodiment wherein receiver 1204 includes an annular groove 1217 and is disposed on at least a portion of a perimeter of housing 1202. In this embodiment, annular groove 1217 may form a recessed portion of receiver 1204. Annular groove 1217 may include a detent engagement portion 1233, for example, a lip, rim, or flange. In this embodiment, receiver 1204 may be configured to engage a connector 1203 including a plurality of flexible extension arms 1236. Flexible arms 1236 may each include a detent portion 1232, such as a tab or a hook, for engagement with detent engagement portion 1233 of annular groove 1217. Upon engagement, flexible extension arms 1236 may elastically deform outwards to accommodate receiver 1204 before "snapping" into an engaged position. For clarity purposes, carrier 1201 is not illustrated in FIG. 7d, Flexible extension arms 1236 of connector 1203 may extend or protrude from carrier 1201.

Figure 7E:
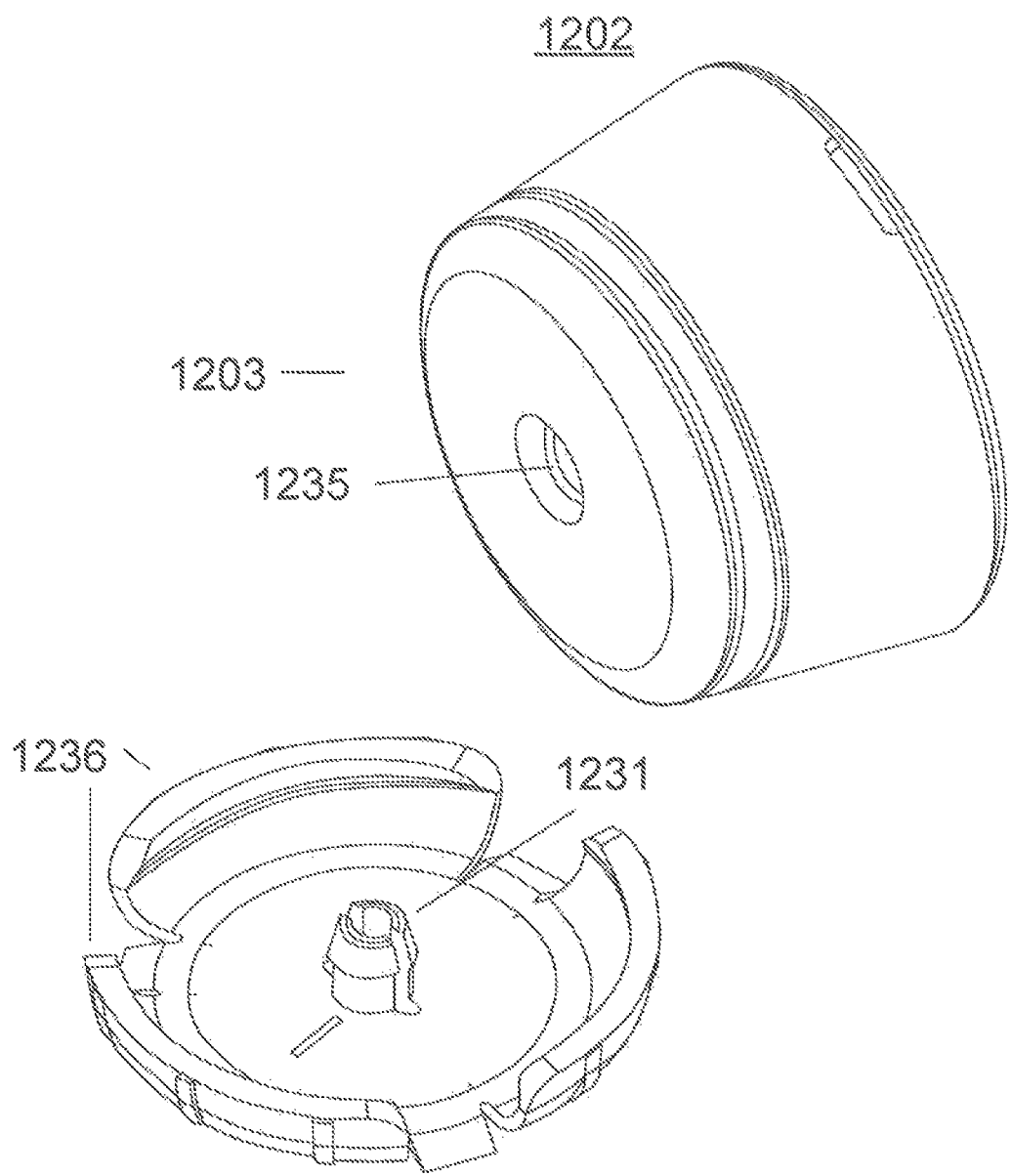

FIG. 7e illustrates an embodiment wherein mechanical connector 1203 features both a central rodlike element 1231 and flexible extension arms 1236 arranged at a perimeter. Both connector 1203 and flexible extension arms 1236 may extend or protrude from carrier 1201 (not illustrated). Rodlike element 1231 may also include flexible extension arms 1234. Either or both of flexible extension arms 1236 and 1234 may include detent portions 1232. Receiver 1204, in this embodiment, may include a plurality of recessed portions, for example, both a centrally located concavity 1235 and a peripherally located annular groove 1217 of housing 1202. Either or both of annular groove 1217 and concavity 1235 may include detent engagement portions 1233 to engage detent portions 1232 of extension arms 1236 and/or extension arms 1234, respectively. Upon engagement, retention of housing 1202 may be secured by either or both of the engagement between rodlike element 1231 and concavity 1235 and the engagement between extension arms 1236 and annular groove 1217. Extension arms 1234 and 1236 may be configured to elastically deform to facilitate engagement. In some embodiments, either rodlike element 1231 or flexible arms 1236 do not include detent portions, and function only facilitate alignment of connector 1203 and receiver 1204.

Figure 7F:
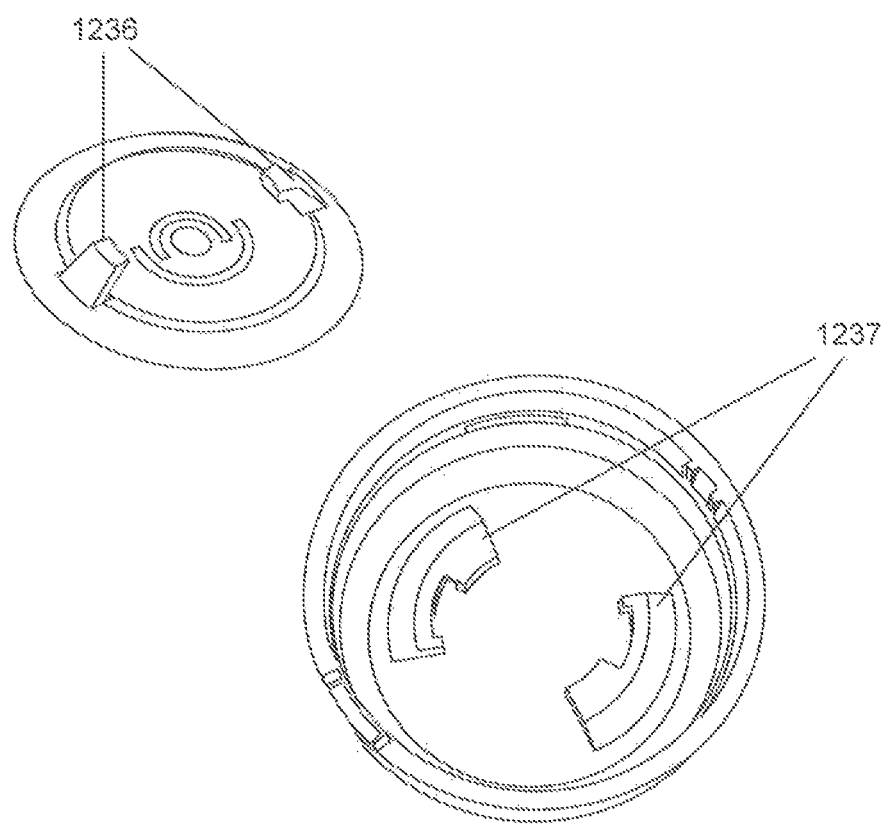

FIG. 7f shows an embodiment configured to engage connector 1203 including a twist-lock connector. As illustrated, receiver 1204 may include a plurality of recesses 1237 including detent engagement portions 1233 while connector 1203 includes a plurality of extension arms 1236 including detent portions 1232. The extension arms 1236 may be configured to be inserted into the recesses 1237 and to securely engage the housing 1202 when the housing 1202 is rotated with respect to the extension arms 1236. Extension arms 1236 of connector 1203 may extend or protrude from carrier 1201 (not illustrated).

The foregoing examples of embodiments of receiver 1204 and connector 1203 are provided for exemplary purposes only. The exemplary embodiments discuss various combinations of features that provide a releasable engagement between carrier 1201 and housing 1202. In alternative embodiments, the various features described may be combined in different ways. For example, while the embodiments discussed in the foregoing generally include a receiver 1204 disposed on a housing 1202 and a connector 1203 disposed on a carrier 1201, this arrangement may be reversed. That is, receiver 1204 may be located on carrier 1201 and connector 1203 may be located on housing 1202. In such embodiments, connector 1203 and receiver 1204 may include any or all of the features discussed above with respect to connector 1203 and receiver 1204. For example, connector 1203 may be a protrusion extending from housing 1202, and receiver 1204 may include recessed portion or concavity of carrier 1201. In such an arrangement, connector 1203 may be configured to engage and be retained within the recessed portion or concavity of receiver 1204. In such an arrangement at least a portion of a sidewall 1251 and a top surface 1252 of housing 1202 may be exposed when the housing is mounted on the flexible adhesive patch.

Implant unit 110 may additionally include a plurality of field-generating implant electrodes 158a, 158b. The electrodes may include any suitable shape and/or orientation on the implant unit so long as the electrodes may be configured to generate an electric field in the body of a patient. Implant electrodes 158a and 158b may also include any suitable conductive material (e.g., copper, silver, gold, platinum, iridium, platinum-iridium, platinum-gold, conductive polymers, etc.) or combinations of conductive (and/or noble metals) materials. In some embodiments, for example, the electrodes may include short line electrodes, circular electrodes, and/or circular pairs of electrodes. As shown in FIG. 8, electrodes 158a and 158b may be located on an end of a first extension 162a of an elongate arm 162. The electrodes, however, may be located on any portion of implant unit 110. Additionally, implant unit 110 may include electrodes located at a plurality of locations, for example on an end of both a first extension 162a and a second extension 162b of elongate arm 162, as illustrated, for example, in FIG. 9. Implant electrodes may have a thickness between about 200 nanometers and 1 millimeter. Anode and cathode electrode pairs may be spaced apart by about a distance of about 0.2 mm to 25 mm. In additional embodiments, anode and cathode electrode pairs may be spaced apart by a distance of about 1 mm to 10 mm, or between 4 mm and 7 mm. Adjacent anodes or adjacent cathodes may be spaced apart by distances as small as 0.001 mm or less, or as great as 25 mm or more. In some embodiments, adjacent anodes or adjacent cathodes may be spaced apart by a distance between about 0.2 mm and 1 mm.

FIG. 8 provides a representation of an exemplary configuration of implant unit 110. As illustrated in FIG. 8, in one embodiment, the field-generating electrodes 158a and 158b may include two sets of four circular electrodes, provided on flexible carrier 161, with one set of electrodes providing an anode and the other set of electrodes providing a cathode. Implant unit 110 may include one or more structural elements to facilitate implantation of implant unit 110 into the body of a patient. Such elements may include, for example, elongated arms, suture holes, polymeric surgical mesh, biological glue, spikes of flexible carrier protruding to anchor to the tissue, spikes of additional biocompatible material for the same purpose, etc. that facilitate alignment of implant unit 110 in a desired orientation within a patient's body and provide attachment points for securing implant unit 110 within a body. For example, in some embodiments, implant unit 110 may include an elongate arm 162 having a first extension 162a and, optionally, a second extension 162b. Extensions 162a and 162b may aid in orienting implant unit 110 with respect to a particular muscle (e.g., the genioglossus muscle), a nerve within a patient's body, or a surface within a body above a nerve. For example, first and second extensions 162a, 162b may be configured to enable the implant unit to conform at least partially around soft or hard tissue (e.g., nerve, bone, or muscle, etc.) beneath a patient's skin. Further, implant unit 110 may also include one or more suture holes 160 located anywhere on flexible carrier 161. For example, in some embodiments, suture holes 160 may be placed on second extension 162b of elongate arm 162 and/or on first extension 162a of elongate arm 162. Implant unit 110 may be constructed in various shapes. Additionally, or alternatively, implant unit 110 may include surgical mesh 1050 or other perforatable material. In some embodiments, implant unit may appear substantially as illustrated in FIG. 8. In other embodiments, implant unit 110 may lack illustrated structures such as second extension 162b, or may have additional or different structures in different orientations. Additionally, implant unit 110 may be formed with a generally triangular, circular, or rectangular shape, as an alternative to the winged shape shown in FIG. 8. In some embodiments, the shape of implant unit 110 (e.g., as shown in FIG. 8) may facilitate orientation of implant unit 110 with respect to a particular nerve to be modulated. Thus, other regular or irregular shapes may be adopted in order to facilitate implantation in differing parts of the body.

As illustrated in FIG. 8, secondary antenna 152 and electrodes 158a, 158b may be mounted on or integrated with flexible carrier 161. Various circuit components and connecting wires (discussed further below) may be used to connect secondary antenna with implant electrodes 158a and 158b. To protect the antenna, electrodes, circuit components, and connecting wires from the environment within a patient's body, implant unit 110 may include a protective coating that encapsulates implant unit 110. In some embodiments, the protective coating may be made from a flexible material to enable bending along with flexible carrier 161. The encapsulation material of the protective coating may also resist humidity penetration and protect against corrosion. In some embodiments, the protective coating may include a plurality of layers, including different materials or combinations of materials in different layers FIG. 9 is a view of an alternate embodiment of an implant unit 110, according to an exemplary embodiment of the present disclosure. As illustrated in FIG. 9, implant unit 110 may include a plurality of electrodes, located, for example, at the ends of first extension 162a and second extension 162b. FIG. 9 illustrates an embodiment wherein implant electrodes 158a and 158b include line electrodes.

Returning to FIGS. 2 and 3, external unit 120 may be configured to communicate with implant unit 110. For example, in some embodiments, a primary signal may be generated on primary antenna 150, using, e.g., processor 144, signal source 142, and amplifier 146. More specifically, in one embodiment, power source 140 may be configured to provide power to one or both of the processor 144 and the signal source 142. The processor 144 may be configured to cause signal source 142 to generate a signal (e.g., an RF energy signal). Signal source 142 may be configured to output the generated signal to amplifier 146, which may amplify the signal generated by signal source 142. The amount of amplification and, therefore, the amplitude of the signal may be controlled, for example, by processor 144. The amount of gain or amplification that processor 144 causes amplifier 146 to apply to the signal may depend on a variety of factors, including, but not limited to, the shape, size, and/or configuration of primary antenna 150, the size of the patient, the location of implant unit 110 in the patient, the shape, size, and/or configuration of secondary antenna 152, a degree of coupling between primary antenna 150 and secondary antenna 152 (discussed further below), a desired magnitude of electric field to be generated by implant electrodes 158a, 158b, etc. Amplifier 146 may output the amplified signal to primary antenna 150.

External unit 120 may communicate a primary signal on primary antenna to the secondary antenna 152 of implant unit 110. This communication may result from coupling between primary antenna 150 and secondary antenna 152. Such coupling of the primary antenna and the secondary antenna may include any interaction between the primary antenna and the secondary antenna that causes a signal on the secondary antenna in response to a signal applied to the primary antenna. In some embodiments, coupling between the primary and secondary antennas may include capacitive coupling, inductive coupling, radiofrequency coupling, etc. and any combinations thereof.

Coupling between primary antenna 150 and secondary antenna 152 may depend on the proximity of the primary antenna 152 relative to the secondary antenna. That is, in some embodiments, an efficiency or degree of coupling between primary antenna 150 and secondary antenna 152 may depend on the proximity of the primary antenna to the secondary antenna. The proximity of the primary and secondary antennas may be expressed in terms of a coaxial offset (e.g., a distance between the primary and secondary antennas when central axes of the primary and secondary antennas are co-aligned), a lateral offset (e.g., a distance between a central axis of the primary antenna and a central axis of the secondary antenna), and/or an angular offset (e.g., an angular difference between the central axes of the primary and secondary antennas). In some embodiments, a theoretical maximum efficiency of coupling may exist between primary antenna 150 and secondary antenna 152 when both the coaxial offset, the lateral offset, and the angular offset are zero. Increasing any of the coaxial offset, the lateral offset, and the angular offset may have the effect of reducing the efficiency or degree of coupling between primary antenna 150 and secondary antenna 152.

As a result of coupling between primary antenna 150 and secondary antenna 152, a secondary signal may arise on secondary antenna 152 when the primary signal is present on the primary antenna 150. Such coupling may include inductive/magnetic coupling, RF coupling/transmission, capacitive coupling, or any other mechanism where a secondary signal may be generated on secondary antenna 152 in response to a primary signal generated on primary antenna 150. Coupling may refer to any interaction between the primary and secondary antennas. In addition to the coupling between primary antenna 150 and secondary antenna 152, circuit components associated with implant unit 110 may also affect the secondary signal on secondary antenna 152. Thus, the secondary signal on secondary antenna 152 may refer to any and all signals and signal components present on secondary antenna 152 regardless of the source.

While the presence of a primary signal on primary antenna 150 may cause or induce a secondary signal on secondary antenna 152, the coupling between the two antennas may also lead to a coupled signal or signal components on the primary antenna 150 as a result of the secondary signal present on secondary antenna 152. A signal on primary antenna 150 induced by a secondary signal on secondary antenna 152 may be referred to as a primary coupled signal component. The primary signal may refer to any and all signals or signal components present on primary antenna 150, regardless of source, and the primary coupled signal component may refer to any signal or signal component arising on the primary antenna as a result of coupling with signals present on secondary antenna 152. Thus, in some embodiments, the primary coupled signal component may contribute to the primary signal on primary antenna 150.

Implant unit 110 may be configured to respond to external unit 120. For example, in some embodiments, a primary signal generated on primary coil 150 may cause a secondary signal on secondary antenna 152, which in turn, may cause one or more responses by implant unit 110. In some embodiments, the response of implant unit 110 may include the generation of an electric field between implant electrodes 158a and 158b.

Figure 10:
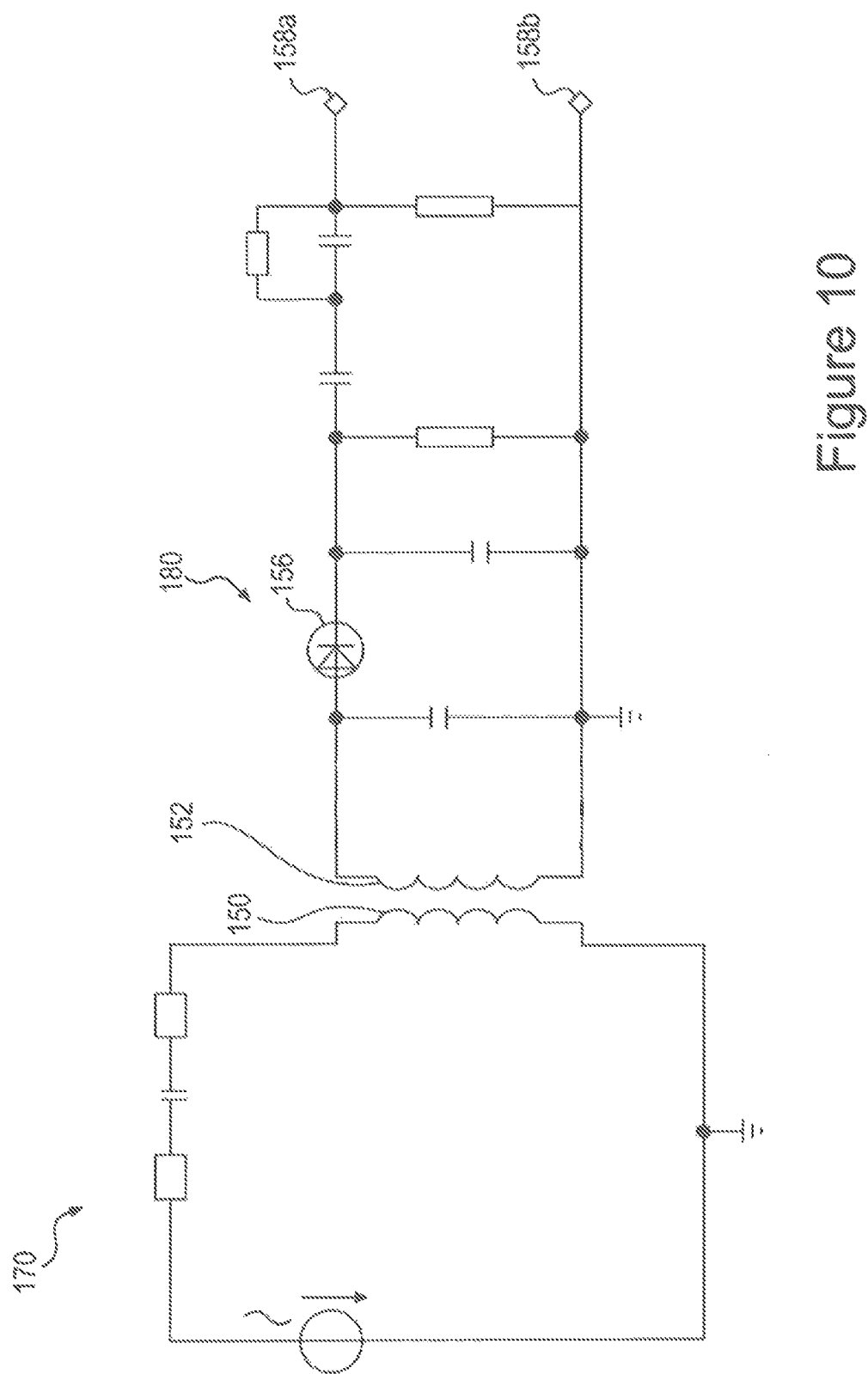
FIG. 10 illustrates circuitry of an implant unit and an external unit, according to an exemplary embodiment of the present disclosure.

FIG. 10 illustrates circuitry 170 that may be included in external unit 120 and circuitry 180 that may be included in implant unit 110. Additional, different, or fewer circuit components may be included in either or both of circuitry 170 and circuitry 180. As shown in FIG. 10, secondary antenna 152 may be arranged in electrical communication with implant electrodes 158a, 158b. In some embodiments, circuitry connecting secondary antenna 152 with implant electrodes 158a and 158b may cause a voltage potential across implant electrodes 158a and 158b in the presence of a secondary signal on secondary antenna 152. This voltage potential may be referred to as a field inducing signal, as this voltage potential may generate an electric field between implant electrodes 158a and 158b. More broadly, the field inducing signal may include any signal (e.g., voltage potential) applied to electrodes associated with the implant unit that may result in an electric field being generated between the electrodes.

The field inducing signal may be generated as a result of conditioning of the secondary signal by circuitry 180. As shown in FIG. 10, circuitry 170 of external unit 120 may be configured to generate an AC primary signal on primary antenna 150 that may cause an AC secondary signal on secondary antenna 152. In certain embodiments, however, it may be advantageous (e.g., in order to generate a unidirectional electric field for modulation of a nerve) to provide a DC field inducing signal at implant electrodes 158a and 158b. To convert the AC secondary signal on secondary antenna 152 to a DC field inducing signal, circuitry 180 in implant unit 110 may include an AC-DC converter. The AC to DC converter may include any suitable converter known to those skilled in the art. For example, in some embodiments the AC-DC converter may include rectification circuit components including, for example, diode 156 and appropriate capacitors and resistors. In alternative embodiments, implant unit 110 may include an AC-AC converter, or no converter, in order to provide an AC field inducing signal at implant electrodes 158a and 158b.

As noted above, the field inducing signal may be configured to generate an electric field between implant electrodes 158a and 158b. In some instances, the magnitude and/or duration of the generated electric field resulting from the field inducing signal may be sufficient to modulate one or more nerves in the vicinity of electrodes 158a and 158b. In such cases, the field inducing signal may be referred to as a modulation signal. In other instances, the magnitude and/or duration of the field inducing signal may generate an electric field that does not result in nerve modulation. In such cases, the field inducing signal may be referred to as a sub-modulation signal.

Various types of field inducing signals may constitute modulation signals. For example, in some embodiments, a modulation signal may include a moderate amplitude and moderate duration, while in other embodiments, a modulation signal may include a higher amplitude and a shorter duration. Various amplitudes and/or durations of field-inducing signals across electrodes 158a, 158b may result in modulation signals, and whether a field-inducing signal rises to the level of a modulation signal can depend on many factors (e.g., distance from a particular nerve to be stimulated; whether the nerve is branched; orientation of the induced electric field with respect to the nerve; type of tissue present between the electrodes and the nerve; etc.).

Whether a field inducing signal constitutes a modulation signal (resulting in an electric field that may cause nerve modulation) or a sub-modulation signal (resulting in an electric field not intended to cause nerve modulation) may ultimately be controlled by processor 144 of external unit 120. For example, in certain situations, processor 144 may determine that nerve modulation is appropriate. Under these conditions, processor 144 may cause signal source 144 and amplifier 146 to generate a modulation control signal on primary antenna 150 (i.e., a signal having a magnitude and/or duration selected such that a resulting secondary signal on secondary antenna 152 will provide a modulation signal at implant electrodes 158a and 158b).

Processor 144 may be configured to limit an amount of energy transferred from external unit 120 to implant unit 110. For example, in some embodiments, implant unit 110 may be associated with a threshold energy limit that may take into account multiple factors associated with the patient and/or the implant. For example, in some cases, certain nerves of a patient should receive no more than a predetermined maximum amount of energy to minimize the risk of damaging the nerves and/or surrounding tissue. Additionally, circuitry 180 of implant unit 110 may include components having a maximum operating voltage or power level that may contribute to a practical threshold energy limit of implant unit 110. Processor 144 may be configured to account for such limitations when setting the magnitude and/or duration of a primary signal to be applied to primary antenna 150.

In addition to determining an upper limit of power that may be delivered to implant unit 110, processor 144 may also determine a lower power threshold based, at least in part, on an efficacy of the delivered power. The lower power threshold may be computed based on a minimum amount of power that enables nerve modulation (e.g., signals having power levels above the lower power threshold may constitute modulation signals while signals having power levels below the lower power threshold may constitute sub-modulation signals).

A lower power threshold may also be measured or provided in alternative ways. For example, appropriate circuitry or sensors in the implant unit 110 may measure a lower power threshold. A lower power threshold may be computed or sensed by an additional external device, and subsequently programmed into processor 144, or programmed into implant unit 110. Alternatively, implant unit 110 may be constructed with circuitry 180 specifically chosen to generate signals at the electrodes of at least the lower power threshold. In still another embodiment, an antenna of external unit 120 may be adjusted to accommodate or produce a signal corresponding to a specific lower power threshold. The lower power threshold may vary from patient to patient, and may take into account multiple factors, such as, for example, modulation characteristics of a particular patient's nerve fibers, a distance between implant unit 110 and external unit 120 after implantation, and the size and configuration of implant unit components (e.g., antenna and implant electrodes), etc.

Processor 144 may also be configured to cause application of sub-modulation control signals to primary antenna 150. Such sub-modulation control signals may include an amplitude and/or duration that result in a sub-modulation signal at electrodes 158a, 158b. While such sub-modulation control signals may not result in nerve modulation, such sub-modulation control signals may enable feedback-based control of the nerve modulation system. That is, in some embodiments, processor 144 may be configured to cause application of a sub-modulation control signal to primary antenna 150. This signal may induce a secondary signal on secondary antenna 152, which, in turn, induces a primary coupled signal component on primary antenna 150.

To analyze the primary coupled signal component induced on primary antenna 150, external unit 120 may include a feedback circuit 148 (e.g., a signal analyzer or detector, etc.), which may be placed in direct or indirect communication with primary antenna 150 and processor 144. Sub-modulation control signals may be applied to primary antenna 150 at any desired periodicity. In some embodiments, the sub-modulation control signals may be applied to primary antenna 150 at a rate of one every five seconds (or longer). In other embodiments, the sub-modulation control signals may be applied more frequently (e.g., once every two seconds, once per second, once per millisecond, once per nanosecond, or multiple times per second). Further, it should be noted that feedback may also be received upon application of modulation control signals to primary antenna 150 (i.e., those that result in nerve modulation), as such modulation control signals may also result in generation of a primary coupled signal component on primary antenna 150.

The primary coupled signal component may be fed to processor 144 by feedback circuit 148 and may be used as a basis for determining a degree of coupling between primary antenna 150 and secondary antenna 152. The degree of coupling may enable determination of the efficacy of the energy transfer between two antennas. Processor 144 may also use the determined degree of coupling in regulating delivery of power to implant unit 110.

Processor 144 may be configured with any suitable logic for determining how to regulate power transfer to implant unit 110 based on the determined degree of coupling. For example, where the primary coupled signal component indicates that a degree of coupling has changed from a baseline coupling level, processor 144 may determine that secondary antenna 152 has moved with respect to primary antenna 150 (either in coaxial offset, lateral offset, or angular offset, or any combination). Such movement, for example, may be associated with a movement of the implant unit 110, and the tissue that it is associated with based on its implant location. Thus, in such situations, processor 144 may determine that modulation of a nerve in the patient's body is appropriate. More particularly, in response to an indication of a change in coupling, processor 144, in some embodiments, may cause application of a modulation control signal to primary antenna 150 in order to generate a modulation signal at implant electrodes 158a, 158b, e.g., to cause modulation of a nerve of the patient.

In an embodiment for the treatment of sleep disordered breathing, movement of an implant unit 110 may be associated with movement of the tongue, which may indicate the onset of a sleep apnea event or a sleep apnea precursor. The onset of a sleep apnea event of sleep apnea precursor may require the stimulation of the genioglossus muscle of the patient to relieve or avert the event. Such stimulation may result in contraction of the muscle and movement of the patient's tongue away from the patient's airway.

In embodiments for the treatment of head pain, including migraines, processor 144 may be configured to generate a modulation control signal based on a signal from a user, for example, or a detected level of neural activity in a sensory neuron (e.g. the greater occipital nerve or trigeminal nerve) associated with head pain. A modulation control signal generated by the processor and applied to the primary antenna 150 may generate a modulation signal at implant electrodes 158a, 158b, e.g., to cause inhibition or blocking of a sensory nerve of the patient. Such inhibition or blocking may decrease or eliminate the sensation of pain for the patient.

In embodiments for the treatment of hypertension, processor 144 may be configured to generate a modulation control signal based on, for example, pre-programmed instructions and/or signals from an implant indicative of blood pressure. A modulation control signal generated by the processor and applied to the primary antenna 150 may generate a modulation signal at implant electrodes 158a, 158b, e.g., to cause either inhibition or stimulation of nerve of a patient, depending on the requirements. For example, a neuromodulator placed in a carotid artery or jugular artery (i.e. in the vicinity of a carotid baroreceptor), may receive a modulation control signal tailored to induce a stimulation signal at the electrodes, thereby causing the glossopharyngeal nerve associated with the carotid baroreceptors to fire at an increased rate in order to signal the brain to lower blood pressure. Similar modulation of the glossopharyngeal nerve may be achieved with a neuromodulator implanted in a subcutaneous location in a patient's neck or behind a patient's ear. A neuromodulator place in a renal artery may receive a modulation control signal tailored to cause an inhibiting or blocking signal at the electrodes, thereby inhibiting a signal to raise blood pressure carried from the renal nerves to the kidneys.

Modulation control signals may include stimulation control signals, and sub-modulation control signals may include sub-stimulation control signals. Stimulation control signals may have any amplitude, pulse duration, or frequency combination that results in a stimulation signal at electrodes 158a, 158b. In some embodiments (e.g., at a frequency of between about 6.5-13.6 MHz), stimulation control signals may include a pulse duration of greater than about 50 microseconds and/or an amplitude of approximately 0.5 amps, or between 0.1 amps and 1 amp, or between 0.05 amps and 3 amps. Sub-stimulation control signals may have a pulse duration less than about 500, or less than about 200 nanoseconds and/or an amplitude less than about 1 amp, 0.5 amps, 0.1 amps, 0.05 amps, or 0.01 amps. Of course, these values are meant to provide a general reference only, as various combinations of values higher than or lower than the exemplary guidelines provided may or may not result in nerve stimulation.

In some embodiments, stimulation control signals may include a pulse train, wherein each pulse includes a plurality of sub-pulses. An alternating current signal (e.g., at a frequency of between about 6.5-13.6 MHz) may be used to generate the pulse train, as follows. A sub-pulse may have a duration of between 50-250 microseconds, or a duration of between 1 microsecond and 2 milliseconds, during which an alternating current signal is turned on. For example, a 200 microsecond sub-pulse of a 10 MHz alternating current signal will include approximately 2000 periods. Each pulse may, in turn, have a duration of between 100 and 500 milliseconds, during which sub-pulses occur at a frequency of between 25 and 100 Hz. For example, a 200 millisecond pulse of 50 Hz sub-pulses will include approximately 10 sub-pulses. Finally, in a pulse train, each pulse may be separated from the next by a duration of between 0.2 and 2 seconds. For example, in a pulse train of 200 millisecond pulses, each separated by 1.3 seconds from the next, a new pulse will occur every 1.5 seconds. A pulse train of this embodiment may be utilized, for example, to provide ongoing stimulation during a treatment session. In the context of sleep disordered breathing, a treatment session may be a period of time during which a subject is asleep and in need of treatment to prevent sleep disordered breathing. Such a treatment session may last anywhere from about three to ten hours. In the context of other conditions to which neural modulators of the present disclosure are applied, a treatment session may be of varying length according to the duration of the treated condition.

Processor 144 may be configured to determine a degree of coupling between primary antenna 150 and secondary antenna 152 by monitoring one or more aspects of the primary coupled signal component received through feedback circuit 148. In some embodiments, processor 144 may determine a degree of coupling between primary antenna 150 and secondary antenna 152 by monitoring a voltage level associated with the primary coupled signal component, a current level, or any other attribute that may depend on the degree of coupling between primary antenna 150 and secondary antenna 152. For example, in response to periodic sub-modulation signals applied to primary antenna 150, processor 144 may determine a baseline voltage level or current level associated with the primary coupled signal component. This baseline voltage level, for example, may be associated with a range of movement of the patient's tongue when a sleep apnea event or its precursor is not occurring, e.g. during normal breathing. As the patient's tongue moves toward a position associated with a sleep apnea event or its precursor, the coaxial, lateral, or angular offset between primary antenna 150 and secondary antenna 152 may change. As a result, the degree of coupling between primary antenna 150 and secondary antenna 152 may change, and the voltage level or current level of the primary coupled signal component on primary antenna 150 may also change. Processor 144 may be configured to recognize a sleep apnea event or its precursor when a voltage level, current level, or other electrical characteristic associated with the primary coupled signal component changes by a predetermined amount or reaches a predetermined absolute value.

Figure 11:
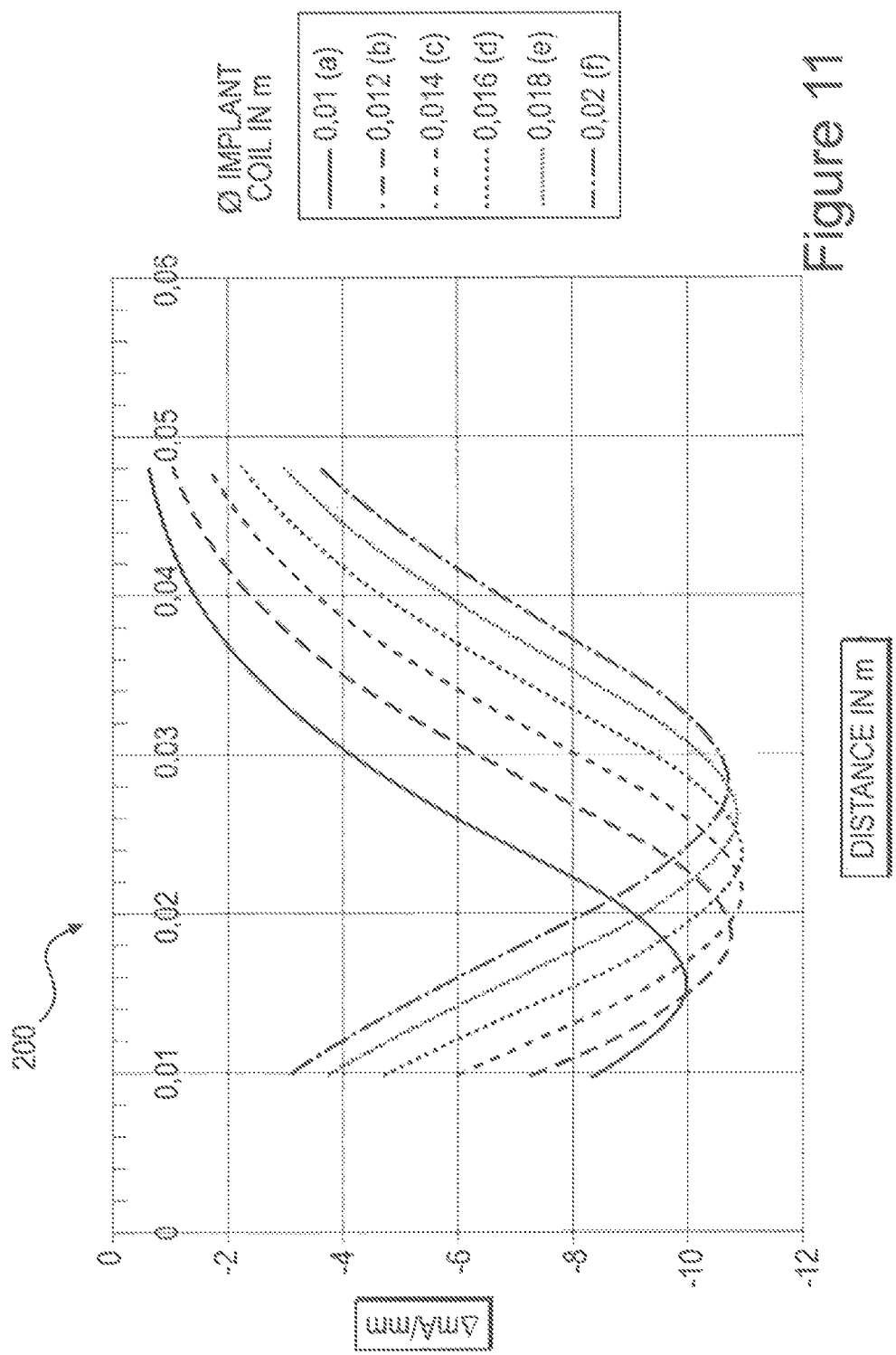
FIG. 11 illustrates a graph of quantities that may be used in determining energy delivery as a function coupling, according to an exemplary disclosed embodiment.

FIG. 11 provides a graph that illustrates this principle in more detail. For a two-coil system where one coil receives a radio frequency (RF) drive signal, graph 200 plots a rate of change in induced current in the receiving coil as a function of coaxial distance between the coils. For various coil diameters and initial displacements, graph 200 illustrates the sensitivity of the induced current to further displacement between the coils, moving them either closer together or further apart. It also indicates that, overall, the induced current in the secondary coil will decrease as the secondary coil is moved away from the primary, drive coil, i.e. the rate of change of induced current, in mA/mm, is consistently negative. The sensitivity of the induced current to further displacement between the coils varies with distance. For example, at a separation distance of 10 mm, the rate of change in current as a function of additional displacement in a 14 mm coil is approximately −6 mA/mm. If the displacement of the coils is approximately 22 mm, the rate of change in the induced current in response to additional displacement is approximately −11 mA/mm, which corresponds to a local maximum in the rate of change of the induced current. Increasing the separation distance beyond 22 mm continues to result in a decline in the induced current in the secondary coil, but the rate of change decreases. For example, at a separation distance of about 30 mm, the 14 mm coil experiences a rate of change in the induced current in response to additional displacement of about −8 mA/mm. With this type of information, processor 144 may be able to determine a particular degree of coupling between primary antenna 150 and secondary antenna 152, at any given time, by observing the magnitude and/or rate of change in the magnitude of the current associated with the primary coupled signal component on primary antenna 150.

In some embodiments, an initially detected coupling degree may establish a baseline range when the patient attaches external unit 120 to the skin. Presumably, while the patient is awake, the tongue is not blocking the patient's airway and moves with the patients breathing in a natural range, where coupling between primary antenna 150 and secondary antenna 152 may be within a baseline range. A baseline coupling range may encompass a maximum coupling between primary antenna 150 and secondary antenna 152. A baseline coupling range may also encompass a range that does not include a maximum coupling level between primary antenna 150 and secondary antenna 152. Thus, the initially determined coupling may be fairly representative of a non-sleep apnea condition and may be used by processor 144 as a baseline in determining a degree of coupling between primary antenna 150 and secondary antenna 152.

As the patient wears external unit 120, processor 144 may periodically scan over a range of primary signal amplitudes to determine current values related to coupling. If a periodic scan results in determination of a degree of coupling different from the baseline coupling, processor 144 may determine that there has been a change from the baseline initial conditions.

By periodically determining a degree of coupling value, processor 144 may be configured to determine, in situ, appropriate parameter values for the modulation control signal that will ultimately result in nerve modulation. For example, by determining the degree of coupling between primary antenna 150 and secondary antenna 152, processor 144 may be configured to select characteristics of the modulation control signal (e.g., amplitude, pulse duration, frequency, etc.) that may provide a modulation signal at electrodes 158a, 158b in proportion to or otherwise related to the determined degree of coupling. In some embodiments, processor 144 may access a lookup table or other data stored in a memory correlating modulation control signal parameter values with degree of coupling. In this way, processor 144 may adjust the applied modulation control signal in response to an observed degree of coupling.

Additionally or alternatively, processor 144 may be configured to determine the degree of coupling between primary antenna 150 and secondary antenna 152 during modulation. The tongue, or other structure on or near which the implant is located, and thus implant unit 110, may move as a result of modulation. Thus, the degree of coupling may change during modulation. Processor 144 may be configured to determine the degree of coupling as it changes during modulation, in order to dynamically adjust characteristics of the modulation control signal according to the changing degree of coupling. This adjustment may permit processor 144 to cause implant unit 110 to provide an appropriate modulation signal at electrodes 158a, 158b throughout a modulation event. For example, processor 144 may alter the primary signal in accordance with the changing degree of coupling in order to maintain a constant modulation signal, or to cause the modulation signal to be reduced in a controlled manner according to patient needs.

More particularly, the response of processor 144 may be correlated to the determined degree of coupling. In situations where processor 144 determines that the degree of coupling between primary antenna 150 and secondary antenna has fallen only slightly below a predetermined coupling threshold (e.g, during snoring or during a small vibration of the tongue or other sleep apnea event precursor), processor 144 may determine that only a small response is necessary. Thus, processor 144 may select modulation control signal parameters that will result in a relatively small response (e.g., a short stimulation of a nerve, small muscle contraction, etc.). Where, however, processor 144 determines that the degree of coupling has fallen substantially below the predetermined coupling threshold (e.g., where the tongue has moved enough to cause a sleep apnea event), processor 144 may determine that a larger response is required. As a result, processor 144 may select modulation control signal parameters that will result in a larger response. In some embodiments, only enough power may be transmitted to implant unit 110 to cause the desired level of response. In other words, processor 144 may be configured to cause a metered response based on the determined degree of coupling between primary antenna 150 and secondary antenna 152. As the determined degree of coupling decreases, processor 144 may cause transfer of power in increasing amounts. Such an approach may preserve battery life in the external unit 120, may protect circuitry 170 and circuitry 180, may increase effectiveness in addressing the type of detected condition (e.g., sleep apnea, snoring, tongue movement, etc.), and may be more comfortable for the patient.

In some embodiments, processor 144 may employ an iterative process in order to select modulation control signal parameters that result in a desired response level. For example, upon determining that a modulation control signal should be generated, processor 144 may cause generation of an initial modulation control signal based on a set of predetermined parameter values. If feedback from feedback circuit 148 indicates that a nerve has been modulated (e.g, if an increase in a degree of coupling is observed), then processor 144 may return to a monitoring mode by issuing sub-modulation control signals. If, on the other hand, the feedback suggests that the intended nerve modulation did not occur as a result of the intended modulation control signal or that modulation of the nerve occurred but only partially provided the desired result (e.g, movement of the tongue only partially away from the airway), processor 144 may change one or more parameter values associated with the modulation control signal (e.g., the amplitude, pulse duration, etc.).

Where no nerve modulation occurred, processor 144 may increase one or more parameters of the modulation control signal periodically until the feedback indicates that nerve modulation has occurred. Where nerve modulation occurred, but did not produce the desired result, processor 144 may re-evaluate the degree of coupling between primary antenna 150 and secondary antenna 152 and select new parameters for the modulation control signal targeted toward achieving a desired result. For example, where stimulation of a nerve causes the tongue to move only partially away from the patient's airway, additional stimulation may be desired. Because the tongue has moved away from the airway, however, implant unit 110 may be closer to external unit 120 and, therefore, the degree of coupling may have increased. As a result, to move the tongue a remaining distance to a desired location may require transfer to implant unit 110 of a smaller amount of power than what was supplied prior to the last stimulation-induced movement of the tongue. Thus, based on a newly determined degree of coupling, processor 144 can select new parameters for the stimulation control signal aimed at moving the tongue the remaining distance to the desired location.

In one mode of operation, processor 144 may be configured to sweep over a range of parameter values until nerve modulation is achieved. For example, in circumstances where an applied sub-modulation control signal results in feedback indicating that nerve modulation is appropriate, processor 144 may use the last applied sub-modulation control signal as a starting point for generation of the modulation control signal. The amplitude and/or pulse duration (or other parameters) associated with the signal applied to primary antenna 150 may be iteratively increased by predetermined amounts and at a predetermined rate until the feedback indicates that nerve modulation has occurred.

Processor 144 may be configured to determine or derive various physiologic data based on the determined degree of coupling between primary antenna 150 and secondary antenna 152. For example, in some embodiments the degree of coupling may indicate a distance between external unit 120 and implant unit 110, which processor 144 may use to determine a position of external unit 120 or a relative position of a patient's tongue. Monitoring the degree of coupling can also provide such physiologic data as whether a patient's tongue is moving or vibrating (e.g, whether the patient is snoring), by how much the tongue is moving or vibrating, the direction of motion of the tongue, the rate of motion of the tongue, etc.

In response to any of these determined physiologic data, processor 144 may regulate delivery of power to implant unit 110 based on the determined physiologic data. For example, processor 144 may select parameters for a particular modulation control signal or series of modulation control signals for addressing a specific condition relating to the determined physiologic data. If the physiologic data indicates that the tongue is vibrating, for example, processor 144 may determine that a sleep apnea event is likely to occur and may issue a response by delivering power to implant unit 110 in an amount selected to address the particular situation. If the tongue is in a position blocking the patient's airway (or partially blocking a patient's airway), but the physiologic data indicates that the tongue is moving away from the airway, processor 144 may opt to not deliver power and wait to determine if the tongue clears on its own. Alternatively, processor 144 may deliver a small amount of power to implant unit 110 (e.g., especially where a determined rate of movement indicates that the tongue is moving slowly away from the patient's airway) to encourage the tongue to continue moving away from the patient's airway or to speed its progression away from the airway. The scenarios described are exemplary only. Processor 144 may be configured with software and/or logic enabling it to address a variety of different physiologic scenarios with particularity. In each case, processor 144 may be configured to use the physiologic data to determine an amount of power to be delivered to implant unit 110 in order to modulate nerves associated with the tongue with the appropriate amount of energy.

The disclosed embodiments may be used in conjunction with a method for regulating delivery of power to an implant unit. The method may include determining a degree of coupling between primary antenna 150 associated with external unit 120 and secondary antenna 152 associated with implant unit 110, implanted in the body of a patient. Determining the degree of coupling may be accomplished by processor 144 located external to implant unit 110 and that may be associated with external unit 120. Processor 144 may be configured to regulate delivery of power from the external unit to the implant unit based on the determined degree of coupling.

As previously discussed, the degree of coupling determination may enable the processor to further determine a location of the implant unit. The motion of the implant unit may correspond to motion of the body part where the implant unit may be attached. This may be considered physiologic data received by the processor. The processor may, accordingly, be configured to regulate delivery of power from the power source to the implant unit based on the physiologic data. In alternative embodiments, the degree of coupling determination may enable the processor to determine information pertaining to a condition of the implant unit. Such a condition may include location as well as information pertaining to an internal state of the implant unit. The processor may, according to the condition of the implant unit, be configured to regulate delivery of power from the power source to the implant unit based on the condition data.

In some embodiments, implant unit 110 may include a processor located on the implant. A processor located on implant unit 110 may perform all or some of the processes described with respect to the at least one processor associated with an external unit. For example, a processor associated with implant unit 110 may be configured to receive a control signal prompting the implant controller to turn on and cause a modulation signal to be applied to the implant electrodes for modulating a nerve. Such a processor may also be configured to monitor various sensors associated with the implant unit and to transmit this information back to and external unit. Power for the processor unit may be supplied by an onboard power source or received via transmissions from an external unit.

In other embodiments, implant unit 110 may be self-sufficient, including its own power source and a processor configured to operate the implant unit 110 with no external interaction. For example, with a suitable power source, the processor of implant unit 110 could be configured to monitor conditions in the body of a subject (via one or more sensors or other means), determining when those conditions warrant modulation of a nerve, and generate a signal to the electrodes to modulate a nerve. The power source could be regenerative based on movement or biological function; or the power sources could be periodically rechargeable from an external location, such as, for example, through induction.

Other embodiments of the present disclosure will be apparent to those skilled in the art from consideration of the specification and practice of the present disclosure.

Additional aspects of the invention are described in the following numbered paragraphs, which are part of the description of exemplary embodiments of the invention. Each numbered paragraph stands on its own as a separate embodiment of the invention.

What is claimed is:

1. A device for treating sleep apnea by conveying power from a location external to a subject to a location within the subject, the device comprising:
   a flexible carrier shaped to facilitate placement between a chin and a neck of the subject adjacent to an internal location of branched fibers of a hypoglossal nerve;
   an adhesive on a first side of the flexible carrier;
   at least one flexible coil of electrically conductive material arranged on the first side of the flexible carrier between the adhesive and the flexible carrier, the at least one flexible coil being configured for use in transmitting power to an implant located to modulate the branched fibers of the hypoglossal nerve, the at least one flexible coil having a plurality of windings; and
   a mechanical connector extending from a second side of the carrier opposite the adhesive, wherein the mechanical connector is configured to be received by and detachably retained by a receiver located on a housing configured for mounting on the flexible carrier,
   wherein
      the mechanical connector is further configured to maintain electrical contact between a power supply of the housing and the at least one flexible coil located on the flexible carrier to enable powering the implant, and the at least one flexible coil is further configured to transmit power to an implant located to modulate terminal fibers of the hypoglossal nerve.

2. The device of claim 1, wherein electrical contact is maintained using at least one electrical connector associated with the flexible carrier.

3. The device of claim 1, wherein the housing is retained in a manner in which at least a portion of a sidewall and a top of the housing is exposed when mounted to the flexible carrier.

4. The device of claim 1, wherein the mechanical connector is a rod like element.

5. The device of claim 1, wherein the receiver includes an opening into which the mechanical connector extends.

6. The device of claim 1, wherein the mechanical connector includes a detent portion.

7. The device of claim 1, wherein the mechanical connector includes a bayonet connection including extending arms configured with receptor slots disposed thereon.

8. The device of claim 1, wherein the mechanical connector includes flexible arms.

9. The device of claim 1, wherein the receiver is disposed on a portion of a perimeter of the housing.

10. The device of claim 1, wherein the mechanical connector includes a plurality of extension arms, the receiver includes a plurality of recesses, and the extension arms are configured to be inserted into the recesses and to securely engage the housing when it is rotated with respect to the extension arms.

11. The device of claim 1, wherein the mechanical connector is configured to break upon removal from the electronics housing.

12. The device of claim 1, further comprising an exposed electrical portion electrically connected to the at least one flexible coil of electrically conductive material, wherein the mechanical connector is configured to maintain contact between an electrical connector of the housing and the exposed electrical portion when received by the electronics housing.

13. The device of claim 12, wherein:
the mechanical connector is adapted to permit relative rotation between the housing and the flexible carrier, and the exposed electrical portion is adapted to maintain contact between the electrical connector of the housing and the exposed electrical portion during rotation of the housing.

14. The device of claim 13, wherein the exposed electrical portion includes two electrodes arranged as concentric circles.

15. The device of claim 1, wherein a portion of the at least one flexible coil is arranged on the second side of the flexible carrier.

16. The device of claim 1, wherein the at least one flexible coil of electrically conductive material is elliptically shaped.

17. The device of claim 1, wherein the plurality of windings creates a pattern that spirals inwardly.

18. A device for treating sleep apnea by conveying power from a location external to a subject to a location within the subject, the device comprising:

a flexible carrier shaped to facilitate placement between a chin and a neck of the subject adjacent to an internal location of branched fibers of a hypoglossal nerve;

an adhesive on a first side of the flexible carrier;

at least one flexible coil of electrically conductive material arranged on the first side of the flexible carrier between the adhesive and the flexible carrier, the at least one flexible coil being configured for use in transmitting power to an implant located to modulate the branched fibers of the hypoglossal nerve, the at least one flexible coil having a plurality of windings, wherein the at least one flexible coil is further configured for use in transmitting power to an implant located to modulate terminal fibers of the hypoglossal nerve from a location spaced apart from the terminal fibers; and a mechanical connector extending from a second side of the carrier opposite the adhesive, wherein the mechanical connector is configured to be received by and retained by a receiver associated with a housing configured for mounting on the carrier.

* * * * *